(12) United States Patent
Zand et al.

(10) Patent No.: US 8,569,074 B2
(45) Date of Patent: Oct. 29, 2013

(54) ANALYTE-RELEASING BEADS AND USE THEREOF IN QUANTITATIVE ELISPOT OR FLUORISPOT ASSAY

(75) Inventors: Martin S. Zand, Rochester, NY (US); Alicia D. Henn, Rochester, NY (US)

(73) Assignee: University of Rochester, Rochester, NY (US)

( * ) Notice: Subject to any disclaimer, the term of this patent is extended or adjusted under 35 U.S.C. 154(b) by 690 days.

(21) Appl. No.: 12/298,626

(22) PCT Filed: Apr. 30, 2007

(86) PCT No.: PCT/US2007/067801
§ 371 (c)(1),
(2), (4) Date: Jul. 29, 2010

(87) PCT Pub. No.: WO2007/127981
PCT Pub. Date: Nov. 8, 2007

(65) Prior Publication Data
US 2010/0297603 A1    Nov. 25, 2010

Related U.S. Application Data

(60) Provisional application No. 60/745,982, filed on Apr. 28, 2006.

(51) Int. Cl.
*G01N 33/543* (2006.01)
(52) U.S. Cl.
CPC .................................. *G01N 33/543* (2013.01)
USPC ............ 436/518; 435/7.1; 435/7.92; 436/501
(58) Field of Classification Search
None
See application file for complete search history.

(56) References Cited

U.S. PATENT DOCUMENTS

| | | | |
|---|---|---|---|
| 5,986,076 | A | 11/1999 | Rothschild et al. |
| 6,165,778 | A | 12/2000 | Kedar |
| 6,348,318 | B1 | 2/2002 | Valkirs |
| 2003/0176409 | A1 * | 9/2003 | Offner .......................... 514/182 |
| 2004/0175696 | A1 | 9/2004 | Ullman et al. |
| 2004/0248100 | A1 | 12/2004 | Myers et al. |

OTHER PUBLICATIONS

Scheibenbogen et al., (Quantitation of antigen-reactive T cells in peripheral blood by IFNy-ELISPOT assay and chromium-release assay, Journal of Immunological Methods, 244 (2000) pp. 81-89.*
He et al., "Ribosome Display of antibodies: Expression, Specificity, and Recovery in Eukaryotic System," J. Imm. Methods, 2005, vol. 297, pp. 73-82.
Smith et al., "Development and Validation of a Gamma Interferon ELISPOT Assay for Quantitation of Cellular Immune Responses to Varicella-zoster Virus," Clin. Diag. Lab. Immun., 2001, vol. 8, No. 5, pp. 871-879.
Pang et al., "Relative Quantification of Experimental Data from antigen particle Arrays," Clin. Chem., 2005, vol. 51, No. 6, pp. 1029-1031.
Roberts, Josh, "Measuring Cytokine Levels: Researchers use ELISAs, beads, and arrays to quantify intercellular communication," The Scientist, 2004, vol. 18, Issue.9, No. 42 (1-7).
Olejnik et al., "Photocleavable Peptide-DNA Conjugates: Synthesis and Applications to DNA Analysis Using MALDI-MS," Nucleic Acids Res., vol. 27, No. 23, pp. 4626-4631, 1999.
International Search Report for corresponding PCT application PCT/US2007/067801, Sep. 5, 2008.

* cited by examiner

*Primary Examiner* — Gary W Counts
(74) *Attorney, Agent, or Firm* — LeClairRyan, a Professional Corporation

(57) ABSTRACT

A method of quantifying analyte secreted by a cell or released from a drug delivery vehicle, typically by ELISpot or fluorispot assay is described. Quantification is possible through the use of an analyte-releasing reagent that includes a bead and the analyte releasably bound to the bead, or a container pre-spotted with analyte released from the reagent. The reagent or pre-spotted containers can be used to provide a standard curve for release of the analyte. By detecting analyte secreted by one or more cells or drug released by a drug delivery vehicle, and comparing the detected analyte to the standard curve, it is possible to quantify the amount of analyte released by the one or more cells or drug released by the drug delivery vehicle. Kits and reagents for practicing the methods of the present invention are also disclosed.

30 Claims, 16 Drawing Sheets

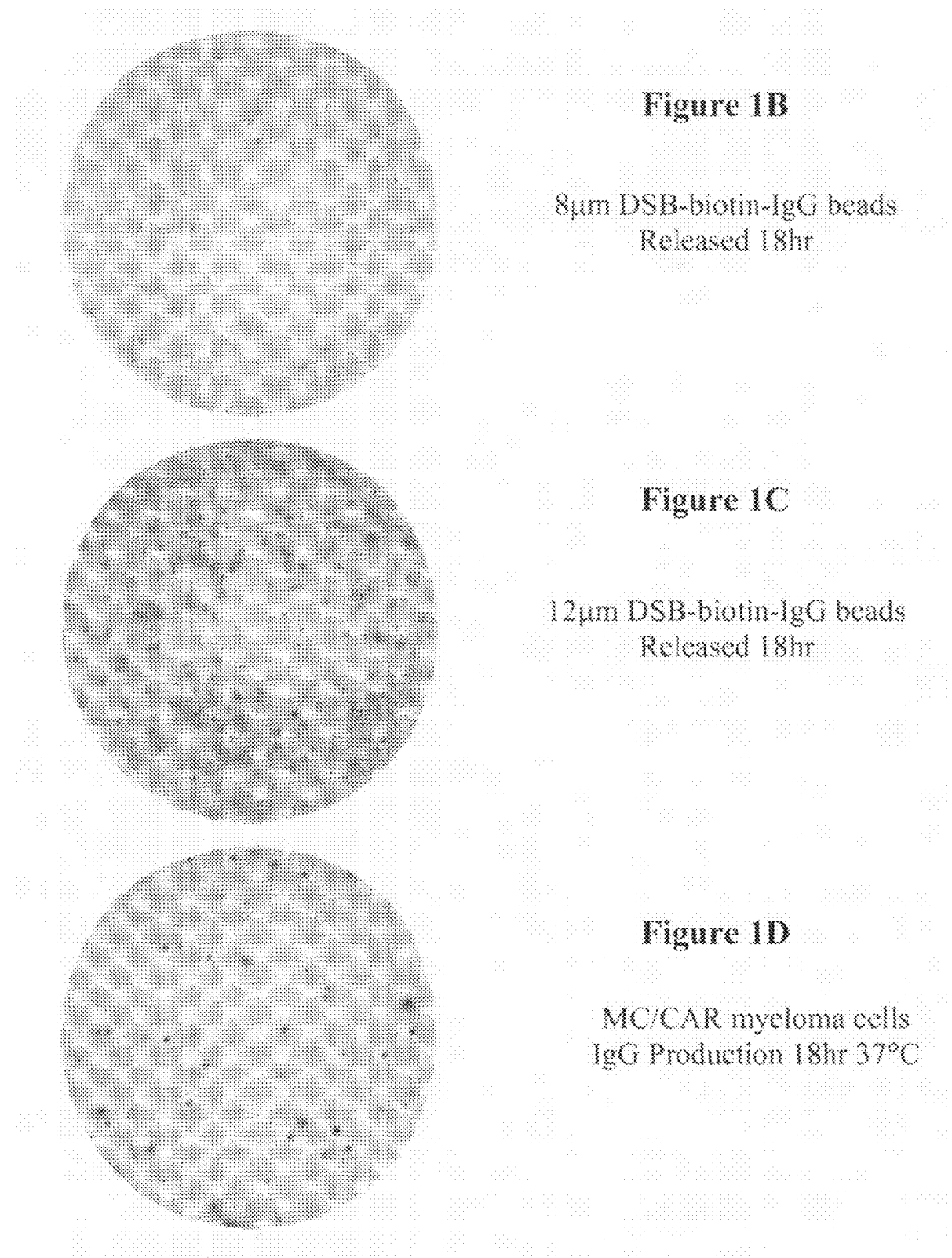

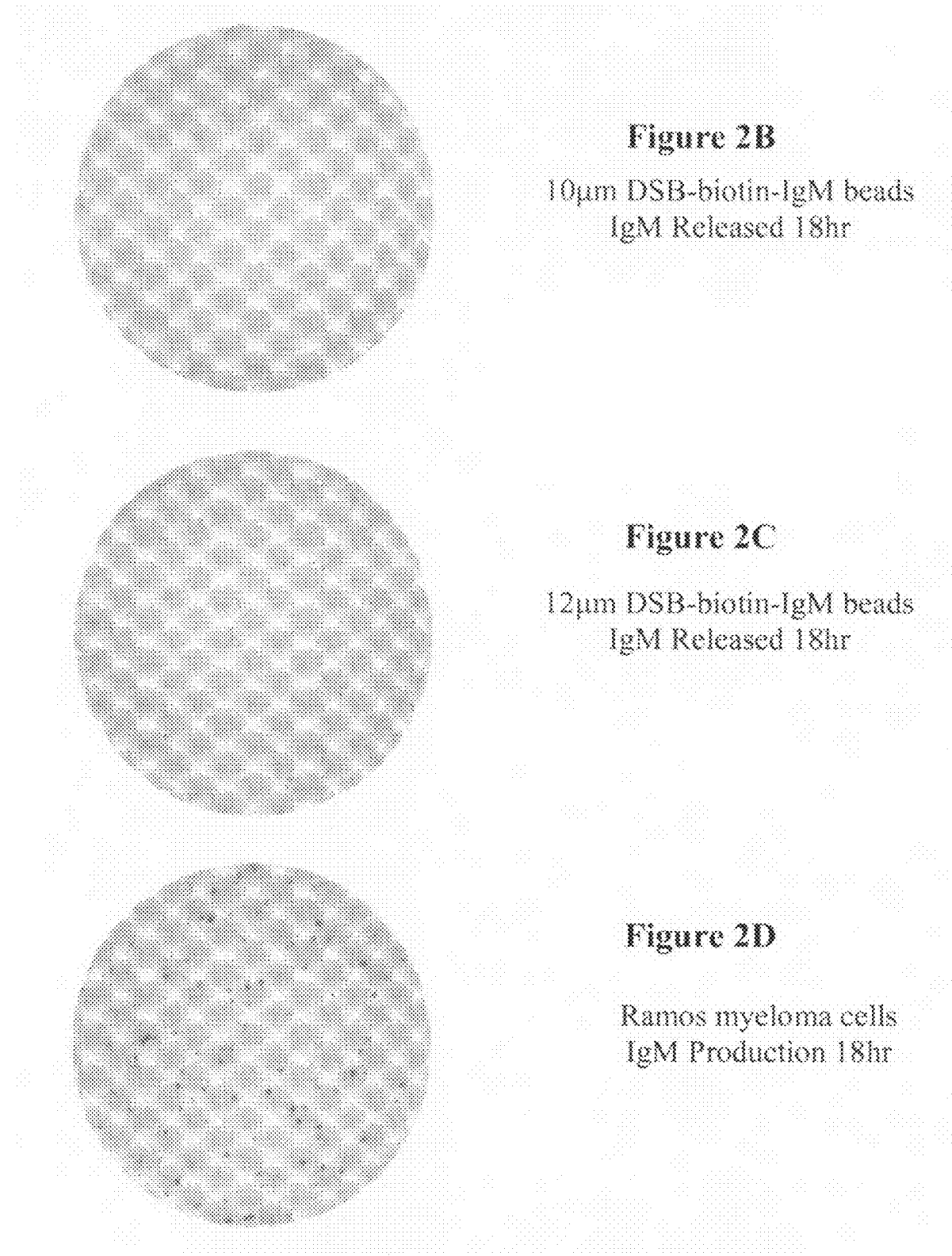

US 8,569,074 B2

ANALYTE-RELEASING BEADS AND USE THEREOF IN QUANTITATIVE ELISPOT OR FLUORISPOT ASSAY

The present application is a national stage application under 35 U.S.C. §371 from PCT Application No. PCT/US2007/067801, filed Apr. 30, 2007, which claims the priority benefit of provisional U.S. Patent Application Ser. No. 60/745,982, filed Apr. 28, 2006.

The present invention was made with government support under grant N01-AI50020 from the National Institutes of Health. The government has certain rights in the invention.

FIELD OF THE INVENTION

The present invention relates to reagents and their use in performing assays for the detection and quantification of biological analytes of interest.

BACKGROUND OF THE INVENTION

ELISpot assays employ the sandwich enzyme-linked immunosorbent assay (ELISA) technique. Either a monoclonal or polyclonal antibody specific for the chosen analyte is typically pre-coated onto a PVDF (polyvinylidene difluoride)-backed microplate. Appropriately stimulated cells are pipetted into the wells and the microplate is placed into a humidified 37° C. $CO_2$ incubator for a specified period of time. During this incubation period, the immobilized antibody, in the immediate vicinity of the secreting cells, binds secreted analyte. After washing away any cells and unbound substances, an antibody specific for the chosen analyte is added to the wells. The detecting antibody can either be biotinylated or it may be conjugated directly to alkaline-phosphatase, horseradish peroxidase, or another enzyme. With the former, additional steps of incubating with enzyme-conjugated-streptavidin and washing are performed. Regardless of the approach, following all wash procedures a substrate solution is added. A colored precipitate forms and appears as spots at the sites of analyte localization, with each individual spot representing an individual analyte-secreting cell. The spots can be counted with an automated ELISpot reader system or manually, using a stereomicroscope.

FLUORIspot assays employ the same general procedures, except that a fluorochrome is conjugated to the detecting antibody (although biotin can be used to amplify the signal produced). This type of detecting antibody omits the need for an enzymatic detection system as described above. Instead, fluorochrome bound to the analyte of interest can be measured directly using a fluorimeter or other appropriate detection devices.

Both of these assays can only provide limited data. They can only enumerate the number of cells producing a particular antigen/analyte. Regardless of the type of assay, neither of these assays is capable of quantifying analyte secreted by the cells. It would be desirable to modify these assays in a manner that can afford analyte quantification.

The present invention is directed to overcoming these and other deficiencies in the art.

SUMMARY OF THE INVENTION

A first aspect of the present invention relates to a method of quantifying cellular secretion of an analyte that includes the steps of: providing a container having a surface capable of binding an analyte; providing a standard curve for release of the analyte into a provided container by one or more analyte-releasing reagents that include a bead and the analyte releasably bound to the bead; introducing into a provided container one or more cells that secrete the analyte; detecting the presence of analyte bound to the surface of the container into which the one or more cells were introduced; and comparing the detected analyte to the standard curve to quantify the amount of analyte released by the one or more cells.

A second aspect of the present invention relates to a method of determining release rates of a drug from a drug delivery vehicle that includes the steps of: providing a container having a surface capable of binding a drug; providing a standard curve for release of the drug into a provided container by one or more drug-releasing reagents that include a bead and the drug releasably bound to the bead; introducing into a provided container a drug delivery vehicle that releases the drug; detecting the presence of drug bound to the surface of the container into which the drug delivery vehicle was introduced; and comparing the detected drug to the standard curve to quantify the amount of drug released by the drug delivery vehicle.

A third aspect of the present invention relates to a kit that includes one or more containers having a surface capable of binding an analyte and either (i) one or more containers pre-spotted with analyte released from one or more analyte-releasing reagents that include a bead and the analyte releasably bound to the bead, or (ii) one or more of the analyte-releasing reagents; and instructions for practicing the method according to the first aspect of the present invention.

A fourth aspect of the present invention relates to a kit that includes one or more containers having a surface capable of binding a drug and either (i) one or more containers pre-spotted with drug released from one or more drug-releasing reagents that include a bead and the drug releasably bound to the bead, or (ii) one or more of the drug-releasing reagents; and instructions for practicing the method according to the second aspect of the present invention.

A fifth aspect of the present invention relates to an analyte-releasing reagent for use in accordance with the first and second aspects of the present invention. The reagent preferably includes: (i) a bead, (ii) a linker molecule including a first portion connected to the bead and a second portion, and (iii) an analyte bound to the second portion of the linker molecule, whereby upon separation of the first and second portions of the linker molecule, the analyte is released from the reagent. In one embodiment, the analyte-releasing reagent is in the form of a mixed population of beads to which the analyte is releasably bound, wherein the mixed population includes at least three different bead populations loaded with different amounts of the analyte. In another embodiment, the analyte-releasing reagent is in the form of a combination of three of more discrete populations of the reagents that are capable of use together to derive a standard curve for analyte release, where each of the populations is loaded with different amounts of the analyte.

A sixth aspect of the present invention relates to a product that includes a container having a surface and analyte, released from an analyte-releasing reagent of the present invention, spotted onto the container surface. The analyte is present as a plurality of spots as a result of exposing the container surface to the analyte-releasing reagent of the present invention under conditions effective to cause release of the analyte by the analyte-releasing reagent. According to one embodiment, the container is in the form of a multi-well plate. According to another embodiment, a combination of three or more discrete containers is provided, where each container is pre-spotted with a different amount of the analyte (i.e., one pre-spotted by reagent loaded with a low amount of analyte, another pre-spotted by reagent loaded with a high amount of analyte, and a third pre-spotted by reagent loaded with an intermediate amount of analyte). This combination of containers can be used to derive a standard curve for analyte release.

Through the use of analyte-release reagents of the present invention, it is possible to generate a standard curve that represents an amount of analyte released from the beads during use. The standard curve can then be used to quantify the amount of the analyte that is secreted or otherwise released from one or more cells during an ELISpot or fluorispot procedure. The use of various combinations of beads having different combinations of linkers and/or polymer coatings allows for different analyte loading onto the analyte-releasing reagents. This allows for the generation of accurate standard curves, which in turn allows for accurate quantification of the analyte of interest.

BRIEF DESCRIPTION OF THE DRAWINGS

FIG. 1A-D shows results for IgG ELISpot assays in a 96 well format. FIG. 1B shows 8 micron desthiobiotin ("DSB")-IgG bead release after 18 hours. FIG. 1C shows 12 micron DSB-biotin-IgG bead release after 18 hours (corresponds to well F-12 of FIG. 1A). FIG. 1D shows MC/CAR myeloma cells IgG secretion after 18 hours at 37° C. (corresponds to well G-6 of FIG. 1A).

FIG. 2A-D shows results for IgM ELISpot assays in a 96 well format. FIG. 2B shows 10 micron DSB-biotin-IgM bead release after 18 hours. FIG. 2C shows 12 micron DSB-biotin-IgM bead release after 18 hours (corresponds to well F-12 of FIG. 2A). FIG. 1D shows Ramos myeloma cell IgM secretion at 18 hours (corresponds to well G-10 of FIG. 1A).

FIG. 6A shows the reduction in mean fluorescence intensity of the beads during release of DSB-IgM with D-biotin as detected using flow cytometric analysis (FIG. 6A). The fluorescence intensity of the beads was compared before release with D-biotin (black histogram), and after two hours of release by D-biotin (grey histogram). The unfilled histogram represents the fluorescence intensity of DSB-IgM-loaded beads stained with isotype control-PE antibody.

FIG. 8A is a graph illustrating the per bead IgG release (in picograms/bead) for uncoated 8 micron polystyrene beads (8-COOH), 8 micron polystyrene beads having a streptavidin-DSB linker (8SA), 10 micron polystyrene beads having a streptavidin-DSB linker (10SA), 3 micron polystyrene beads having a PEG4 coating and streptavidin-DSB linker (3-PEG4), 6 micron polystyrene beads having a PEG4 coating and streptavidin-DSB linker (6-PEG4), 8 micron polystyrene beads having a PEG4 coating and streptavidin-DSB linker (8-PEG4), 8 micron polystyrene beads having a streptavidin functionalized surfaced covered by a PEG4 coating and streptavidin-DSB linker (8SA-PEG4), 10 micron polystyrene beads having a streptavidin functionalized surfaced covered by a PEG4 coating and streptavidin-DSB linker (10SA-PEG4), 3 micron polystyrene beads having a PEG8 coating and streptavidin-DSB linker (3-PEG8), 8 micron polystyrene beads having a PEG8 coating and streptavidin-DSB linker (8-PEG8), 8 micron polystyrene beads having a streptavidin functionalized surfaced covered by a PEG8 coating and streptavidin-DSB linker (8SA-PEG8), and 10 micron polystyrene beads having a streptavidin functionalized surfaced covered by a PEG8 coating and streptavidin-DSB linker (10SA-PEG8). FIG. 8B is a histogram illustrating the distribution of IgG release for MC-CAR myeloma cells and four different types of beads (8SA, 8SA-PEG4, 8-PEG8, and 10SA-PEG4), which together encompass the breadth of the MC-CAR release profile.

DETAILED DESCRIPTION OF THE INVENTION

Figure 1A:
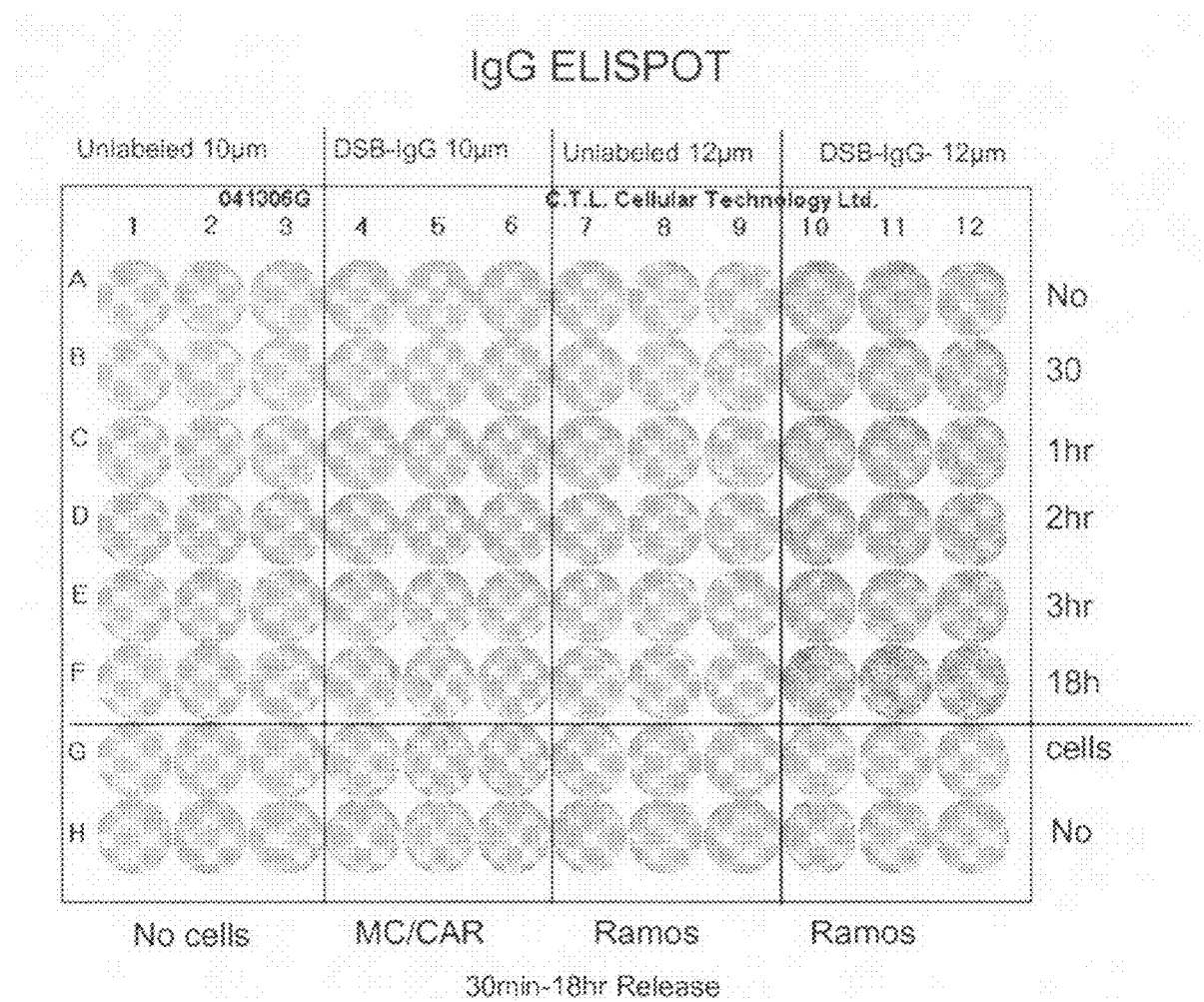
Figure 2A:
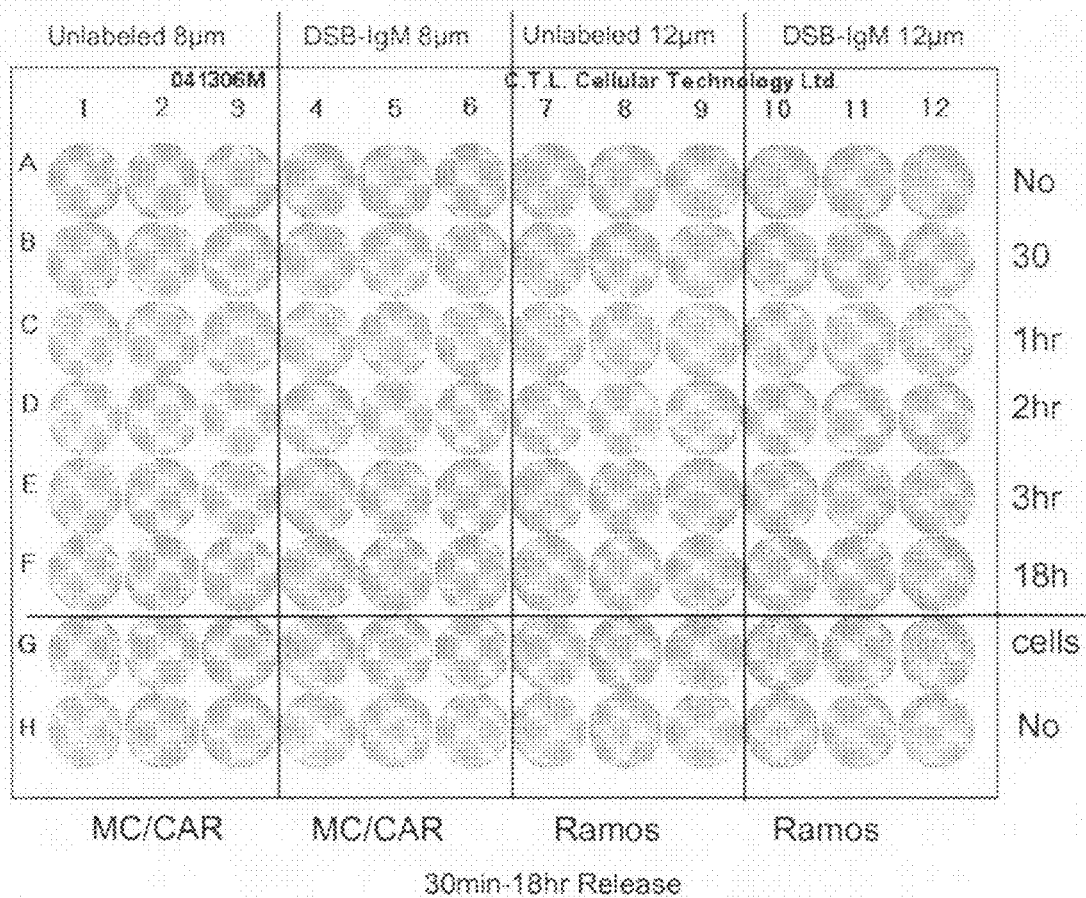

The present invention relates to an improved ELISpot or Fluorispot assay that allows for quantification of antigen/analyte.

One aspect of the present invention relates to a method of quantifying cellular secretion of an analyte. This involves providing a container having a surface capable of binding an analyte, and providing a standard curve for release of the analyte into the provided containers by an analyte-releasing reagent that includes a bead and the analyte releasably bound to the bead. One or more cells that secrete the analyte are introduced into the provided container(s). After allowing a sufficient amount of time for analyte secretion by the one or more cells present in the provided containers, the analyte bound to the surface of the containers can be detected. Analyte detected according to the ELISpot or fluorispot procedures is typically present in the form of a spot, whereby the amount of analyte present contributes to the size and appearance (i.e., color or darkness) of the spot. A comparison is made between the detected analyte (secreted by the one or more cells) and the standard curve to quantify the amount of analyte secreted by the one or more cells.

The standard curve is preferably generated using three or more, preferably four or more, and more preferably five or more different types of analyte-releasing reagents that are characterized by different amounts of analyte loading (on average). The presence of multiple data points for analyte release improves the reliability and accuracy of the standard curve, which improves the accuracy of quantifying analyte secretion by the one or more cells. The standard curve should be generated using the same type of container(s) used to measure analyte release by the cells. In one approach, the standard curve can be provided in the form of software generated previously. In another approach, the user can generate the standard curve prior to analysis of the results of analyte release by the one or more cells. In the latter approach, the user will process reagent in parallel with cells to generate the standard curve.

The standard curve is preferably generated by ELISA, with the wells coated and incubated with analyte-releasing reagent in the same manner as the corresponding ELISpot containers. Basically, the ELISA is carried out using the three or more different types of analyte-releasing reagents that are characterized by different amounts of analyte loading, and the quantity of analyte released by the three or more different reagents is determined by using ELISA standards. The containers can be read on a plate reader, with the optical density values being recorded. By comparing values for analyte released from the reagents to the ELISA standards, the amount of analyte released per bead can be calculated and then used to determine the amount of analyte released by each bead type. Bead spot size and bead analyte release (during ELISA) were compared to form the standard curve. The amount of analyte released by cells can then be compared to the generated standard curve to estimate cellular analyte secretion/release.

As used herein, the term "analyte" refers to any molecule that can be detected by ELISpot or fluorispot procedures. The analyte is preferably any molecule that is capable of being detected in a biological fluid.

According to one embodiment, the analyte is one that is secreted or otherwise released by a cell, including (without limitation) peptides, proteins, enzymes, receptors, hormones, transcription factors, cytokines, chemokines, lymphokines, cytotrophic factors, serum proteins, viral proteins, bacterial proteins, glycoproteins, carbohydrates, lipids, lipid proteins, nucleic acids, small molecules and compounds, tumor antigen, therapeutic chemicals such as antibiotics, interleukins, acute phase response proteins. Analytes may be of plant, animal, viral or bacterial origin (Sherma J., "Thin-layer Chromotography in Food and Agricultural Analysis," *J Chromotogr* 880(1-2):129-47 (2000), which is hereby incorporated by reference in its entirety), and they can be transgenically expressed or naturally expressed.

According to another embodiment, the analyte can be any product to be released by another structure, such as a drug delivery vehicle. For drug delivery vehicles, the methods of the present invention can be used to detect drug release rates/profiles. Drug delivery is described in Coombes et al., "Biodegradable Polymeric Microparticles for Drug Delivery and Vaccine Formulation: The Surface Attachment of Hydrophilic Species Using the Concept of Poly(Ethylene Glycol) Anchoring Segments," *Biomaterials* 18(17):1153-61 (1997), which is hereby incorporated by reference in its entirety.

As used herein, the term "bead" refers to a microparticle of any size, shape, design or construction. In one embodiment, the microparticle can have a shell that defines an interior compartment that carries a predetermine amount of analyte. In another embodiment, the microparticle can have a porous structure, whereby its pores carry a predetermined amount of analyte. In a further embodiment, the microparticle can be either porous or non-porous, because the analyte is loaded substantially entirely onto the external surface of microparticle (i.e., predominantly not within any pores).

The bead (microparticles) can be of any size, but preferably about the size of a cell. Suitable bead sizes include, without limitation, beads of about 0.1 to about 20 microns, preferably between about 8 to about 15 microns.

The bead can be formed of any material to which an analyte can be bound. Suitable materials include, without limitation, a synthetic polymer, biodegradable materials (whether polymeric or non-polymeric), latex, or silica, and the material may also have paramagnetic properties (Shang et al., "Synthesis and Characterization of Paramagnetic Microparticles Through Emulsion-templated Free Radical Polymerization," *Langmuir* 22(6)2516-22 (2006), which is hereby incorporated by reference in its entirety).

One example of a preferred bead material is polystyrene. Polystyrene is a polymer made from the aromatic monomer styrene, a liquid hydrocarbon that is commercially available. At room temperature, polystyrene is normally a solid thermoplastic, but can be melted at higher temperature for molding or extrusion, then resolidified. Polystyrene is described in Piskin et al., "Monosize Microbeads Based on Polystyrene and Their Modified Forms for Some Selected Medical and Biological Applications," *J Biomater Sci Polym Ed* 5(5):451-71 (1994); Vetvicka et al., "Polymer Microbeads in Immunology," *Biomaterials* 8(5):341-5 (1987); and Yap et al., "Assembly of Polystyrene Microspheres and its Application in Cell Micropatterning," *Biomaterials* 28(14):2328-38 (2007), each of which is hereby incorporated by reference in their entirety.

The analyte-releasing reagent can have any one of several constructions.

According to one embodiment, the analyte is applied directly to the bead surface, or formulated structurally into the bead, such that the analyte can be released under selected conditions. Biodegradable beads such as fibrin-based beads (Gorodetsky et al., "Fibrin Microbeads (FMB) as Biodegradable Carriers for Culturing Cells and for Accelerating Wound Healing," *J Investig Dermatol* 112:866-872 (1999), which is hereby incorporated by reference in its entirety), lactide-glycolide polymer (Liu et al., "In vivo Release of Vancomycin from Biodegradable Beads," *J Biomed Mat Red Appl Biomaterials* 63(6):807-813 (2002), which is hereby incorporated by reference in its entirety), albumin beads (Seljelid et al., "Biological Effects of the Immunomodulator β1-3D Polyglucose are Strongly Potentiated by Conjugation to Biodegradable Microbeads," *Scandinavian J Immunol* 45(6):683-687 (1997), which is hereby incorporated by reference in its entirety), gelatin beads (Liu et al., "Autologous Cultured Keratinocytes on Porcine Gelatin Microbeads Effectively Heal Chronic Venous Leg Ulcers," *Wound Repair Regeneration* 12(2):148-156 (2004), which is hereby incorporated by reference in its entirety), hollow calcium phosphate (U.S. Pat. No. 6,358,532 to Starling et al., which is hereby incorporated by reference in its entirety), and hydrogel bead with shell (U.S. Pat. No. 6,358,532 to Starling et al., which is hereby incorporated by reference in its entirety).

According to another embodiment, the analyte is tethered to the bead via a linker molecule. In this embodiment, the linker molecule can have a unitary structure or a binary structure. Regardless of its structure, though, the linker is designed to release the analyte from the bead under selected conditions.

In one approach, the linker has a unitary structure that is cleavable to cause release of the analyte. The cleavage site is between first and second portions of the linker. By way of example and without limitation, the linker can be a peptide or polypeptide having an amino acid sequence that is cleavable by a particular enzyme, the linker can be a double-stranded nucleic acid molecule that is cleavable by a particular restriction endonuclease, or the linker can be a compound having a photocleavable moiety such as photocleavable biotin NHS (available from AmberGen, Inc., Waltham, Mass.) or photocleavable peptide-DNA conjugate (Olejnik et al., "Photocleavable Peptide-DNA Conjugates: Synthesis and Applications to DNA Analysis using MALDI-MS," *Nucl Acids Res* 27(23): 4626-4631 (1999), which is hereby incorporated by reference in its entirety. Other known or hereafter developed cleavable linkers can also be used.

In another approach, the linker can have a binary structure such that first and second portions are bound together under one set of conditions and separable from one another under a second, different set of conditions. The conditions used to cause separation can include a change in the temperature, pH, salt, or presence of an affinity competitor molecule, etc.

One exemplary binary linker includes a pair of single-stranded nucleic acid molecules that are substantially hybridized together at temperatures below the melting temperature of the duplex and substantially single-stranded (i.e., analyte is released) at temperatures above the melting temperature of the duplex. The conditions selected for release preferably result in at least about 85% release, more preferably at least about 90%, most preferably at least about 95%, 97%, 98%, or 99%. As is well known in the art, the melting temperature of a duplex is influenced by the nucleotide sequence itself (e.g., GC content, stacking properties, etc.) and environmental factors (e.g., temperature, salt content, etc.).

Another exemplary binary linker includes a pair of molecules having an affinity for one another. Exemplary binary linkers of this type include, without limitation, biotin and avidin or streptavidin; receptor:ligand pairs such as low-IgE receptor and IgE or low-affinity nerve growth factor receptor and nerve growth factor (Anton et al., "Nerve Growth Factor and Its Low-Affinity Receptor Promote Schwann Cell Migration," *Proc Natl Acad Sci USA* 91:2795-2799 (1994), which is hereby incorporated by reference in its entirety), low-affinity antibody and antigen, lectins and specific carbohydrate molecules (Kijimoto-Ochiai, "CD23 (the low-affinity IgE receptor) as a C-type Lectin: A Multidomain and Multifunctional Molecule," *CMLS* 59(4):648-664 (2002), which is hereby incorporated by reference in its entirety), and hemoglobin with either oxygen or carbon monoxide (Hardison, "A Brief History of Hemoglobins, Plant Animal, Protist, and Bacteria," *Proc Natl Acad Sci USA* 93:5675-5679 (1996), which is hereby incorporated by reference in its entirety). Separation of linker molecules can be induced by the presence of a competitor that has a higher affinity for one of the affinity linker molecules than its original paired linker molecule. The examples of the application demonstrate use of the biotin derivative DSB, paired with avidin or streptavidin, as the binary linkers. In comparison to biotin, DSB has a lower affinity for avidin or streptavidin, and therefore is released from avidin or streptavidin in the presence of biotin.

Another exemplary binary linker includes a pair of electrostatically associated molecules. Exemplary binary linkers of this type include, without limitation, calbindinD 9k and calcium (Spassov et al., "Electrostatic Coupling to pH-titrating Sites as a Source of Cooperativity in Protein-ligand Binding," *Protein Sci* 7:2012-2025 (1998), which is hereby incorporated by reference in its entirety), and alcohol liver dehydrogenase and zinc (Andersson et al., "Electrostatic Field Effects of Coenzymes on Ligand Binding to Catalytic Zinc in Liver Alcohol Dehydrogenase," *Eur J Biochem* 138 (3):603-609 (1984), which is hereby incorporated by reference in its entirety).

Separation of electrostatically associated binary linkers can be controlled by manipulation of pH conditions, such as through the use of appropriate buffers and the addition of acid or base.

Regardless whether the linker has a binary or unitary structure, the analyte can be bound to the second portion of the linker and the bead can be bound to the first portion of the linker using standard coupling chemistries. Several examples are provided in the examples of the present invention.

The analyte-releasing reagent can also include a polymer coating that substantially surrounds the bead. The polymer coating, when present, can have the effect of increasing analyte loading on each bead. This is typically achieved by increasing the number of sites, per bead, where the analyte or analyte-linker can be coupled. If the polymer coating is employed, then the first portion of the linker can be coupled to the polymer, which itself encapsulates the bead.

Any polymer capable of achieving this effect can be utilized. Exemplary polymers for use in coating the bead include, without limitation, polyethylene glycol, dextran, chitosan, acrylamide, cellulose, methacrylate, oxazoline, methacryloxyethyltrimethylammonium, methylpyridine, cinylpyridine, allylamine, butadiene/maleic acid, polyethylene oxide, vinylpyrrolidone, polystyrene, polyvinyl acetate, polyethylenimine, polypropylene, and pullalan.

Of these, polyethylene glycol ("PEG") having a molecular weight of about 20,000 to about 100,000 is preferred. Particularly preferred polyethylene glycol includes pentaerythritol tetra(aminopropyl) polyoxyethylene (a ~20,000 kDa, 4-branched polyethylene glycol) and hexglycerol octa(succinimidyloxyglutaryl)polyoxyethylene (a ~23,000 kDa, 8-branched polyethylene glycol). PEG polymers are described in Croy et al., "Polymeric Micelles for Drug Delivery," *Curr Pharm Des* 12(36):4669-84 (2006); Tessmar et al., "Customized PEG-derived Copolymers for Tissue-engineering Applications," *Macromol Biosci* 7(1):23-39 (2007); Torchilin, "Lipid-core Micelles for Targeted Drug Delivery," *Curr Drug Deliv* 2(4):319-27 (2005), each of which is hereby incorporated by reference in its entirety.

The container used for analyte capture may be in a single or multi-well format. Detectable results may be obtained with or without a capture molecule to bind the analyte of interest. Thus, in certain embodiments of the present invention the surface of the container can be capable of adsorbing the analyte directly, while in other embodiments of the present invention the surface of the container can be provided with a capture molecule that can selectively bind the analyte of interest.

Any suitable capture molecule can be utilized for this purpose. Exemplary capture molecules include, without limitation, antibodies, antibody mimics, high affinity binders, antigens, peptides, proteins, lipids, polysaccharides, oligonucleotides, nucleic acids (e.g., cDNA, cRNA, mRNA), protein-binding ligands, receptors, small molecules, chemical compounds, cell fragments, cellular substructures, synapses, cell organelles, cancer cells, tissue samples, viruses, bacteria, or other microbes.

Antibodies suitable for use as capture molecules include, without limitation, polyclonal antibodies, monoclonal antibodies, chimeric antibodies, single chain antibodies, synthetic antibodies, and any antibody fragments, e.g., Fab fragments, Fab' fragments, F(ab)$_2$ fragments, F(ab')$_2$ fragments, Fd fragments, Fv fragments, dAb fragments, and isolated complementarity determining regions ("CDRs") (see U.S. Pat. Nos. 7,037,498, 7,034,121, 7,041,870, and 7,074,405, which are hereby incorporated by reference in their entirety). These antibody fragments can be made by conventional procedures, such as proteolytic fragmentation procedures, as described in J. Goding, *Monoclonal Antibodies: Principles and Practice*, pp. 98-118 (N.Y. Academic Press 1983), which is hereby incorporated by reference in its entirety. Methods for preparing antibodies that are specific to an analyte of interest are well known in the art. In many embodiments, the binding affinity of an immobilized capture molecule to the respective analyte is at least $10^4$ $M^{-1}$, $10^5$ $M^{-1}$, $10^6$ $M^{-1}$, $10^7$ $M^{-1}$, $10^8$ $M^-$, or stronger.

Numerous methods are available for immobilizing capture molecules to a surface. In many embodiments, the capture molecules are attached to the surface through an adhesion promoting layer: There are several ways in which this layer can be formed. One way is to silanize the sensing surface to form a layer of silane molecules and another way is to use a self-assembled monolayer (SAM). There are further methods available for immobilizing capture molecules, such as chemical modification of the sensing surface with reactive groups and the capture molecules with appropriate linkers (Maskos and Southern, *Nucleic Acids Res.* 20:1679-84 (1992), which is hereby incorporated by reference in its entirety); modification of the surface and capture molecules with photoreactive linkers/groups (see WO 98/27430 to Hubbell and WO 91/16425 to Sigrist, each of which is hereby incorporated by reference in its entirety), immobilization via coulombic interaction (see EP0472990 A2 to Decher, which is hereby incorporated by reference in its entirety), or coupling via tags in chelating reactions.

During performance of the ELISpot or fluorispot assays of the present invention, the analyte-releasing beads can be used in a number of different ways.

According to one approach, the analyte-releasing beads are used in parallel with cells of interest, at the same time, and under the same or similar conditions. In other words, the standard curve is generated in parallel with cell testing. Preferably at least three different bead populations, characterized by different loading of analyte, are used to generate the standard curve. According to another approach, the analyte-releasing beads can be used to pre-spot a container surface prior to introduction of cells of interest into a separate (un-spotted) container. In other words, the standard curve can be generated using the pre-spotted containers in parallel with cell testing. Preferably at least three different containers are used (characterized by different amounts of analyte pre-spotting, e.g., formed using three or more different bead populations loaded with different amounts of analyte) to generate the standard curve.

Any suitable detectable label can be used to detect the presence of the analyte bound to the surface of the container. The detectable label can be conjugated to a secondary reagent, which can be of the same or similar type as the capture molecules described above. Preferred secondary reagents are antibodies, antibody mimics, and antibody fragments of the type described above, or other compounds which bind to the analyte of interest at high affinity. Exemplary detectable labels include, without limitation, fluorescent labels, chemi-luminescent labels, bio-luminescent labels, enzyme labels, and radioactive labels. Suitable fluorescent labels for tagging reagents according to the method of the invention may be selected from the general categories of fluorescent dyes, including, but not limited to, fluoresceins, rhodamines, cyanine dyes, coumarins, and the BODIPY groups of fluorescent dyes. Examples of bioluminescent detectable labels are to be found in the fluorescent reporter proteins, such a Green Fluorescent Protein (GFP) and aequorin. Alternative labels for providing a detectable signal can be fluorescence energy transfer labels.

Any suitable detection equipment can be used to measure the signal afforded by the detection label chosen. Exemplary detectors include, without limitation, ELISpot reader, fluorimeter, stereomicroscope, and high quality flat-bed scanner.

ELISpot assays detect secreted analytes of cells and typically employ the sandwich enzyme-linked immunosorbent assay (ELISA) technique (although the examples herein demonstrate that the analyte can be detected without the need for a capture molecule). Either a monoclonal or polyclonal antibody (or any of the above-identified fragments) specific for the chosen analyte is pre-coated onto a container surface. Cells or analyte-release reagents are introduced into the containers and the containers are placed into a humidified 37° C. $CO_2$ incubator for a specified period of time. During this incubation period, immobilized capture antibody, in the immediate vicinity of the secreting cells or analyte-releasing reagent, binds secreted analyte. After washing away any cells, analyte-releasing reagent, and unbound substances, a detecting antibody specific for the chosen analyte is added to the containers. The detecting antibody can provided with one of the above-described detection labels. Detecting antibody that binds the analyte (bound to the container) reveals individual spots through the detectable label, and each spot represents an individual analyte-secreting cell or analyte-releasing reagent. The spots produced by the one or more cells can be counted with an automated ELISpot reader system or manually, using a stereomicroscope. This data may then be compared to the standard curve generated using the analyte-releasing reagent to quantify the analyte secreted by the one or more cells.

FLUORIspot assays differ from ELISpot assays in that a fluorochrome is conjugated to the detection label. This type of detection label omits the need for an enzymatic detection system as described above. Instead, fluorochrome bound to the analyte of interest can be measured directly using a fluorimeter or other appropriate detection devices.

To analyze ELISpot image data, any appropriate scanning instrument and software suite can be utilized. A high quality flat-bed scanner and suitable scanning software are preferred, because minimal manipulation is required to scan a plate image. Suitable plate images can usually be generated using neutral settings at high resolution. The generated images can be analyzed by analysis software to create individual well images, and then analyze spot count, area, and total intensity for each of the well images. Exemplary analysis software includes ExploraSpot (Rebhahn et al., "Automated Analysis of Two- And Three-Color Fluorescent Elispot (Fluorispot) Assays For Cytokine Secretion," Center for Biodefense Immune Modeling Conference, Jun. 22-23, 2006), which objectively quantifies morphological parameters of each spot (size, intensity, location, and circularity), and then exports the data in FCS format, which can be converted into histograms by conventional flow cytometry software such as FLOWJO™ (Tree Star, Inc., Ashland, Oreg.). ExploraSpot was supplied by the laboratory of Timothy R. Mossman (University of Rochester, Rochester, N.Y.). Any appropriate data analysis software can be utilized to analyze the results, including without limitation SCION IMAGE™ (Scion Corporation, Frederick, Md.) and EXCEL™ (Microsoft Corp, Redmond, Wash.).

EXAMPLES

The following examples are provided to illustrate embodiments of the present invention but are by no means intended to limit its scope.

Example 1

Preparation of Immunoglobulin-Releasing Reagent

Construction of Beads:
Beads were obtained from commercial bead makers such as Bangs Laboratories or Micromod. Materials used to make such beads include latex, polymer, and silica, and the beads may contain iron oxide to give the beads a paramagnetic nature. Bead sizes included 8 microns, 10 microns, and 12 microns (polystyrene, catalog #UMC3N Compel™ Magnetic COOH-modified, polystyrene, catalog #CP01N SuperAvidin Coated Microspheres, Bangs Laboratories), 10 microns (latex, #08-19-104 Micromod, GmbH) and 12 microns (latex, #08-19-124, Micromod, GmbH) in diameter. They are permanently coated with Streptavidin protein, which can bind biotin protein.

DSB-X-Biotin-Antigen Conjugation:
A DSB-X-biotin Protein Labeling Kit (D20655, Molecular Probes, Inc.) was used to conjugate human IgG (Sigma-Aldrich, Inc) to DSB-X biotin. DSB-X biotin is a derivative of desthiobiotin, which is a stable biotin pre-cursor, and has a lower binding affinity for avidin or streptavidin proteins than fully-formed D-biotin. Conjugation was carried out according to manufacturer's directions. Briefly, DSB-X biotin succinimidyl ester in a solution of sodium bicarbonate was combined with purified antibody and allowed to react for 1 hour at room temperature. Conjugated antibody was separated from unconjugated DSB-X biotin with a spin column.

Antigen Bead Coating:
The streptavidin-coated beads were incubated with a solution of DSB-X biotin-conjugated IgG for 30 minutes at room temperature. Any unbound antigen was washed away. The beads were then ready to be counted and used in an ELISpot assay.

Example 2

Preparation of Immunoglobulin-Releasing Magnetic Microparticles

Wash:
For magnetic beads, a slightly different protocol was used. Example 1 is modified as follows. 10 µl aliquots of beads were washed in 500 µl PBS and then placed in a magnet-rack and allowed to settle against the tube. Then the supernatant was carefully removed. The beads were resuspended in 500 µl PBS and allowed to settle. This step was repeated. Antigen solutions were prepared as described in Example 1.

Label:
The supernatant was carefully removed, and then the tubes were carefully removed from the magnet-rack. The beads were resuspended in antigen solution and incubated for 30 minutes.

Wash:
The beads were placed in the magnet-rack and allowed to settle against the tube, and then the supernatant was carefully removed. The beads were resuspended in 500 µl PBS and allowed to settle. This step was repeated. The beads were then ready to be counted and used in an ELISpot assay.

Example 3

ELISpot Assay for Immunoglobulin Secreting Cells

ELISpot Assay was carried out according to the procedure described below. Materials and reagents that were used included Millipore PVDF 96-well multiscreen ELISpot plates, RPMI Cell Culture Medium (Gibco, Inc.), Fetal Bovine Serum (FBS), Pen/Strep, Bovine Serum Albumin (BSA) (powder), Fraction V Sigma A4059-1006, 1× Phosphate Buffered Saline (PBS), Strepavidin-Alkaline Phosphatase (Southern Biotech #7100-04), Vector Alkaline Phosphatase substrate kit III, 70% ethyl alcohol, and Immunospot ELISpot Analyzer (CTL Corp.).

The reagents were prepared as follows. 1×PBS composed of 40 g NaCl, 1 g KCl, 5.75 g $Na_2HPO_4.7H_2O$, 1 g $KH_2PO_4$, 5 L $ddH_2O$ was mixed thoroughly. The capture antibody was prepared at 10 µg/ml in PBS (see Table 1 below). The cell culture medium was prepared using sterile technique, RPMI plus 10% Fetal Bovine Serum with penicillin/streptomycin. PBS and 2% BSA (100 ml+2 gm BSA) was prepared. The detecting antibody was prepared in PBS and 2% BSA at the dilution indicated in Table 1 below. Streptavidin-alkaline phosphatase was prepared (10 ml/plate) and diluted 1:1000 in PBS and BSA. Phosphate buffered saline plus 0.1% TWEEN-20® detergent (TPBS) wash buffer was prepared with PBS and 0.1% TWEEN-20® detergent (v/v).

TABLE 1

Capture and Detection Antibodies IgG, IgM, and IgE Analyte

| Analyte | Capture | Detection (dilution) |
| --- | --- | --- |
| IgG | Biosource AHI0301 | Jackson 109-065-098 (1:750) |
| IgM | Biosource AHI0601 | Biosource AHI1609 (1:300) |
| IgE | Southern Biotech 9240-01 | Southern Biotech 9350-08 (1:500) |

Coat Plate:
The plates were coated with capture antibody solution using a multi-channel pipette by dispensing 50 µl of the coating reagent solutions into wells. The bottom of plate was tapped firmly against the bench to ensure the coating reagent covers the wells. The plates were incubated at room temperature for 4 hours to overnight. Any unused coated plates were stored at 4° C.

Block Plate:
In the Biosafety Cabinet, the plate was rinsed 3 times with cell culture medium, removing residual liquid by gently tapping the plate face down onto absorbent material. 200 µl of cell culture medium was added to each well, the plate was covered and incubated ≥1 hours at 37° C. Then the cell culture medium was removed.

Culture Cells:
Cell culture medium alone (no cells) was added to one set of wells. Then ficoll separates dead cells from live cells (standard operating procedure). Known numbers of live cells were cultured in appropriate wells overnight at 37° C. 5% $CO_2$ without disturbing stacking or disturbing plates. The plates were washed 6 times with 200 µl/well of TPBS. As a final step, the plate was tapped on paper towels to remove excess buffer. Surface decontaminate plate with 70% ethanol.

Antigen Detection:

The detecting antibody was diluted and added to each plate at 100 µl/well. Then the plate was covered and incubated 2 hrs at room temperature. The plates were washed 3 times with TPBS.

Streptavidin-AP:

The Strepavidin was diluted 1:1000 in PBS and BSA. 100 µl per well was added. Then the plate was covered and incubated at room temperature for 30 minutes. The plates were washed 3 times with TPBS. Then the well sealer on the back of the plate was removed and the plate was soaked and submerged in TPBS for 1 hr at room temperature. As a final step, the plate was tapped on paper towels to remove excess buffer. Then the plate back was replaced, pressing to seal around the wells.

Add Substrate and Develop:

The AP substrate was prepared using 2 drops reagent 1 per 5 ml PBS, with mixing, then 2 drops Reagent 2, with mixing, then 2 drops of reagent 3, with mixing. Reagents 1, 2, and 3 are part of a commercial kit from Vector Labs called AP Substrate III (cat #SK-5300). 100 µl/well substrate was added to the plate, followed by incubation for 30 minutes at room temperature in the dark. The plate was rinsed with tap water, with removal of the plate back during the rinse. The plate was dried overnight at room temperature in the dark, and read on a CTL plate reader.

Data Analysis and Interpretation:

When read on the plate reader, the negative control cells should be negative for spots. Positive control cells should make spots. If one or more of these conditions were not met, then the data was considered invalid.

This protocol describes the procedure for performing an assay for human IgG or IgM antibody-producing cells, but other antigens could be detected using different reagents. A 96-well ELISPOT plate (like Millipore Multiscreen HTS #MSHA S4W 10), which contains polyvinylidene fluoride membrane at the bottom of each well, was used. The DSB-X-biotin-IgG beads were added at the same step (FIG. 5, step (1)) as when cells were added. They were added to wells already coated with capture antibody (such as Biosource #AHI0301 anti-human IgG) and blocked from non-specific protein binding. During antigen release from beads or antigen secretion by cells, the antigen was captured on the membrane in the well bottom by the capture antibody.

Figure 5:
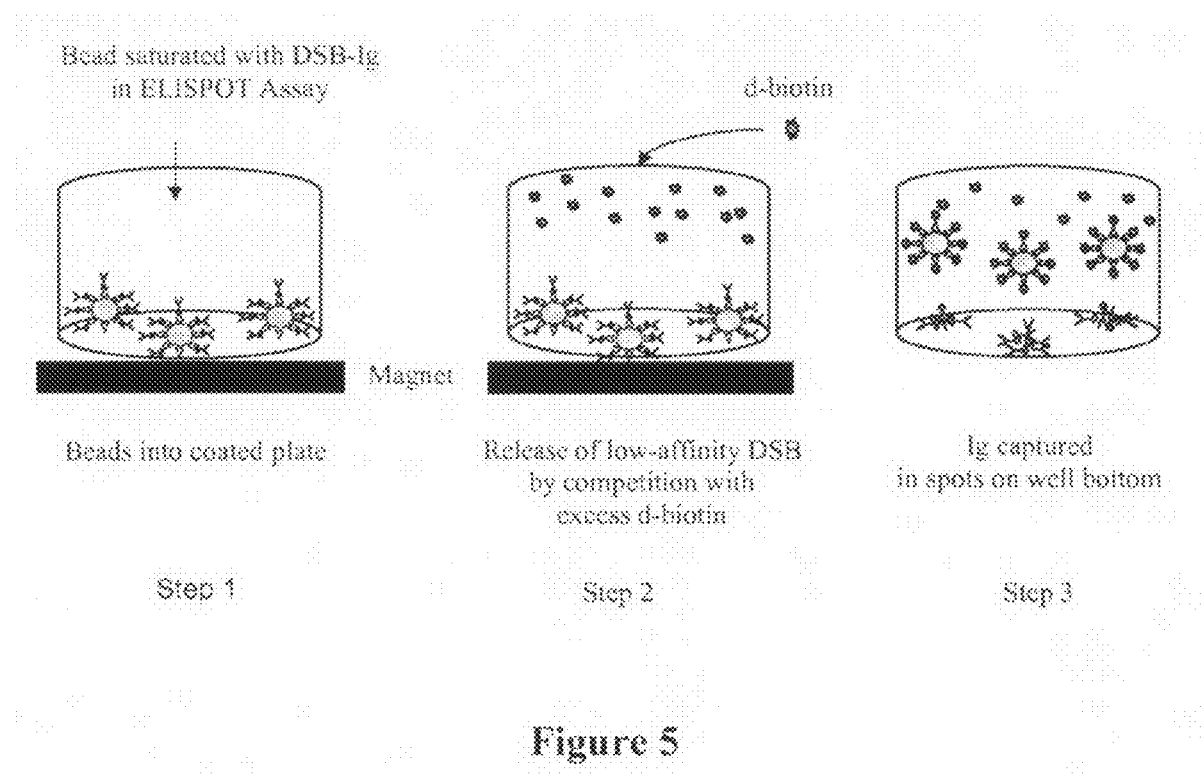
FIG. 5 shows a schematic diagram for the protocol for the release of Ig from a paramagnetic Ig-releasing reagent of the present invention.

Antigen Release:

Antigen release is illustrated schematically in FIG. 5. After beads settled to the bottom of the wells, D-biotin was added to the wells in molar excess to compete off the DSB-antigen (FIG. 5, step (2)). A magnet was used to settle the magnetic beads to the bottom of the wells quickly and immobilize them while the D-biotin was added and the DSB-analyte released.

After antigen release, the cells and beads were washed away from their respective wells (FIG. 5, step (3)), and the spots left by them were visualized. A biotinylated antibody specific for the antigen, like Goat-anti-human IgG-biotin (Jackson Immunoresearch Labs, catalog #109-065-098), was incubated in the wells. In this case, the biotin was used solely to bind to a visualizing enzyme such as streptavidin-conjugated alkaline phosphatase (SA-AP, Southern Biotech #7100-04). Excess reagents were washed away. The remaining alkaline phosphatase bound to the spots turns a substrate (Alkaline Phosphatase Substrate Kit III, Vector Laboratories) into a blue product that precipitates onto the membrane. Permanent blue spots are left where the cells or beads released the analyte of interest (IgG, IgM, IgE).

Quantitation:

The spots were recorded and analyzed using an Immuno-Spot Analyzer (CTL Technologies, LLC). The number of spots, spot size distribution, and other critical spot parameters were analyzed using software such as Scion Image and Excel. Initial results for the IgG ELISpot are shown in FIGS. 1A-D. The largest spots were obtained with 12 µm beads coated with DSB-IgG. Initial results for the IgM ELISpot are shown in FIGS. 2A-D. The largest spots were obtained with 12 µm beads coated with DSB-IgM.

Figure 3:
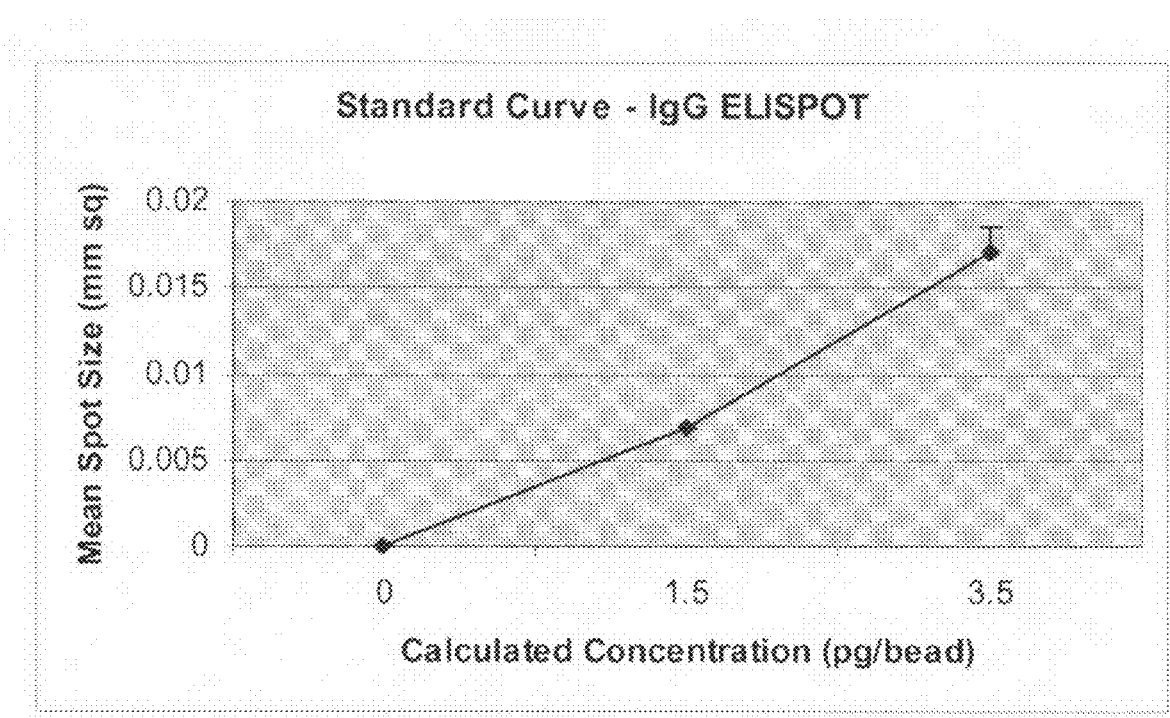
FIG. 3 is a graph illustrating a standard curve for IgG ELISpot that was generated with three reagents loaded with different amounts of IgG (one sample containing unlabeled beads, and two samples having 8 micron beads loaded with different amounts of DSB-IgG). The standard curve was generated by assessing the mean spot sizes and a calculated amount of DSB-IgG bound to the beads. The standard curve correlates the spot size to the amount of DSB-IgG released. The detected mean spot size for MC/CAR myeloma cells, an IgG-producing cell line, correlates to the mean amount of secreted IgG.

Standard Curve Generation:

Spots can be seen in the IgG-specific and IgM-specific ELISPOT assays (FIGS. 1A-D and 2A-D, respectively), indicating the presence of released DSB-IgG or DSB-IgM. Spots of different sizes are produced by antigen released from different sized beads and different amounts of released antigen. Using the mean spot sizes and a calculated amount of DSB-Ig bound to the beads, a standard curve was made relating the spot size to the amount of DSB-Ig released. The standard curve for IgG is shown in FIG. 3, along with the mean spot size (0.0135 mm$^2$) produced by MC/CAR cells, an IgG-producing myeloma cell line. This mean spot size was comparable to about 2.5 pg IgG secreted.

Figure 4:
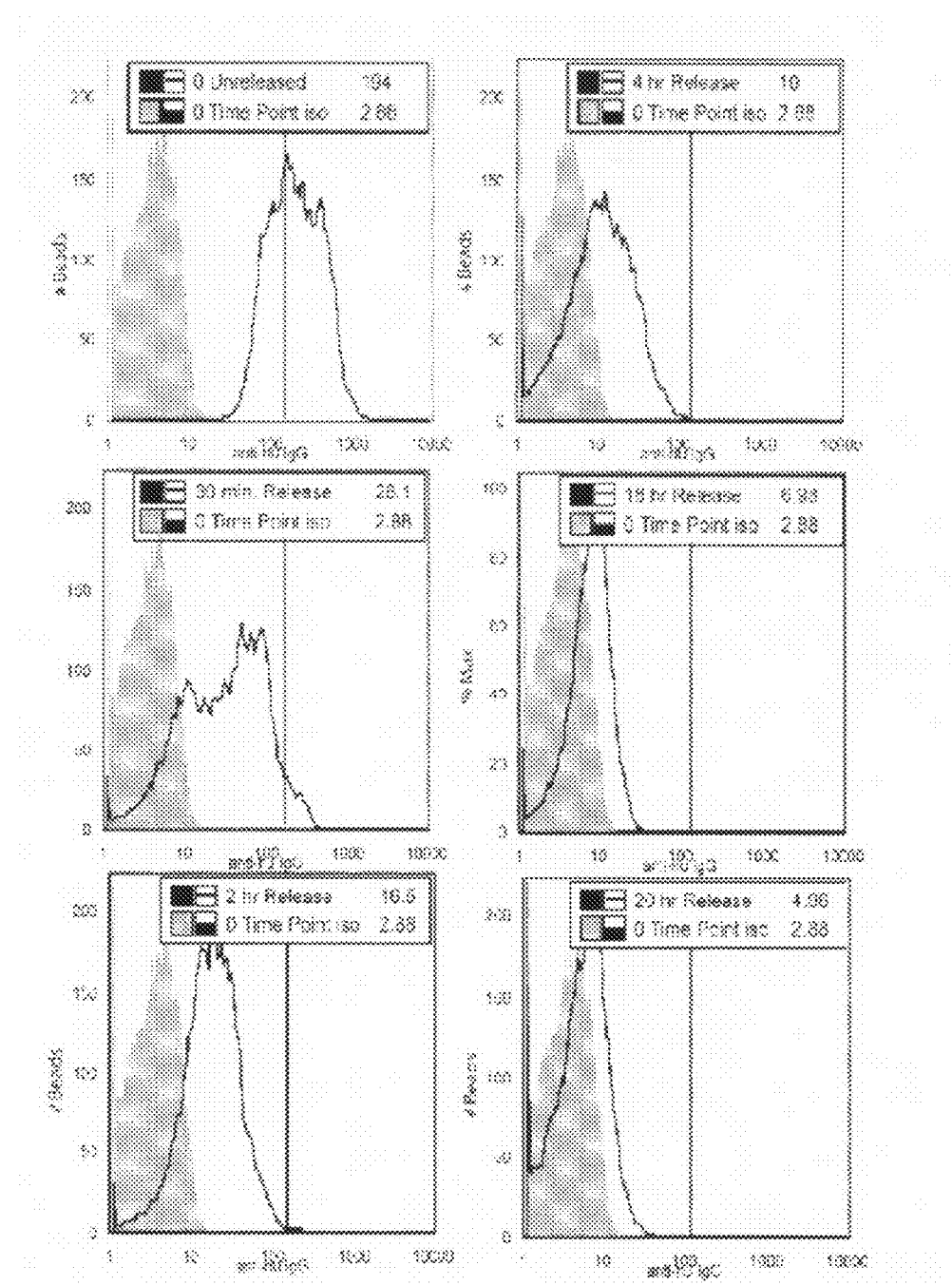
FIG. 4 contains various histograms showing antigen release profiles from DSB-IgG 8 micron beads at 37° C. This time course study demonstrates that D-biotin successfully competes from the low-affinity DSB-Ig from the beads. Release was detected with an anti-human IgG antibody conjugated to phycoerythrin (anti-IgG-PE). The histogram representing the fluorescence of the beads shifts further to the left with increasing time during the incubation, indicating that DSB-Ig elutes from the beads.

Antigen Release Profiles from DSB-IgG- and DSB-IgM:

D-biotin successfully competed with the low-affinity DSB-antigen from the beads. This was demonstrated by labeling the beads at several timepoints during the release with an anti-human IgG antibody conjugated to phycoerythrin (anti-IgG-PE). The histograms of FIG. 4 illustrate that the fluorescence of the beads shifts further to the left with increasing time during the incubation, indicating that DSB-IgG and DSB-IgM were eluting from the beads.

Example 4

IgM Bead Release for ELISpot

Figure 6A:
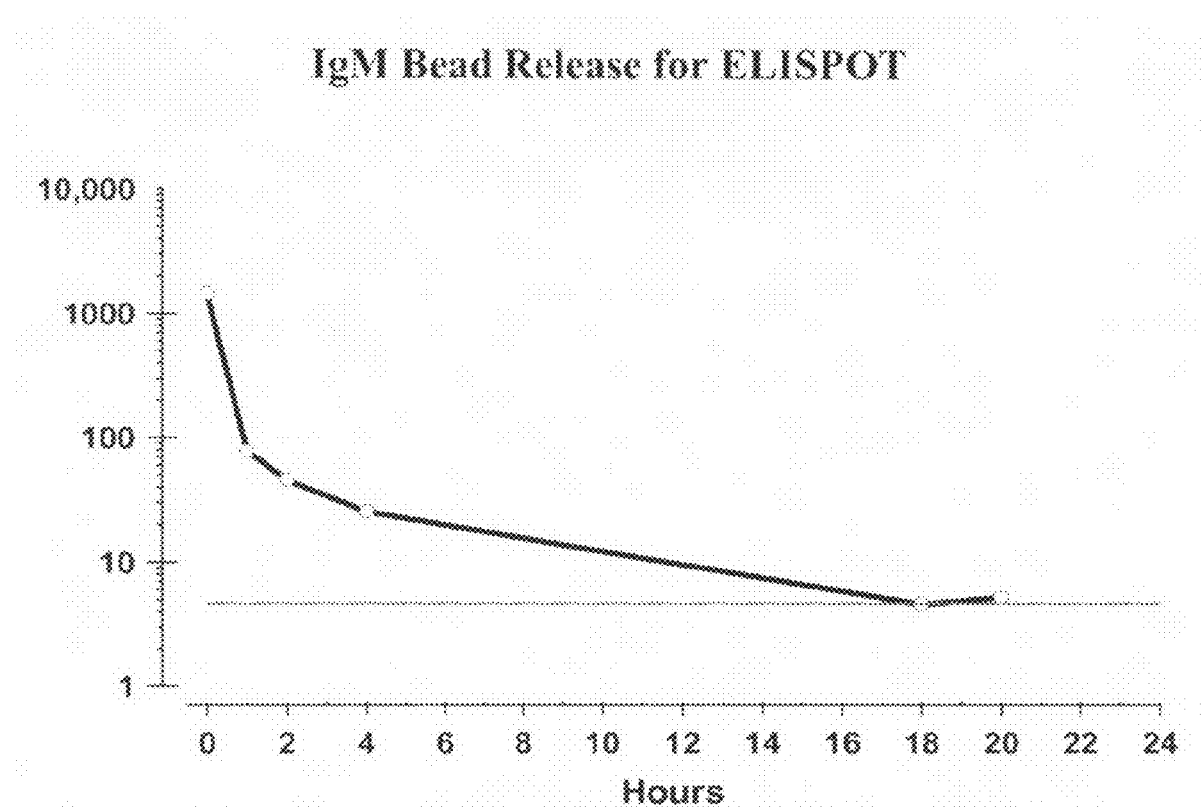
FIGS. 6A-B show IgM bead release for ELISpot. Polymer streptavidin-coated beads were loaded with DSB-conjugated IgM and stained with anti-IgM-PE (phycoerythrin).
Figure 6B:
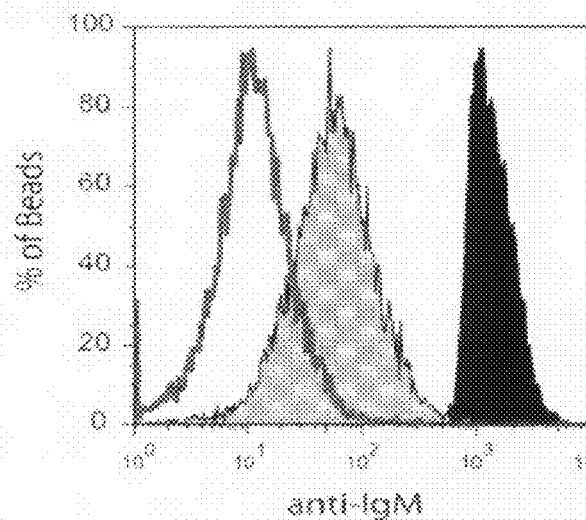

Streptavidin-coated 8 micron beads were coated with desthiobiotin (DSB)-conjugated IgM protein. Streptavidin has a lower binding affinity for DSB, a biotin precursor, than for biotin. The beads were incubated with an excess of normal D-biotin to compete off the DSB-IgM. Anti-IgM-PE and a flow cytometer was used to measure DSB-IgM still bound to the beads during release (FIG. 6A). A change in the mean fluorescence intensity can be seen over time (FIG. 6B).

Example 5

Preparation of Immunoglobulin-Releasing Reagent Having Magnetic Microparticles

Magnetic beads were labeled with a low affinity DSB-Ig conjugate, which was then placed into the ELISpot assay where a stronger affinity biotin, D-biotin was added to compete off the conjugate. A known quantity of Ig was released to create standard spots for comparison in ELISpot making it a more quantitative rather than qualitative assay.

Wash Preparation:

No more than 10$^5$ beads of each bead size were suspended in 500 µl PBS+2% BSA. The tubes were placed on a magnet, and the beads were allowed to adhere to the side for 5 minutes. The supernatant was removed and resuspend by gentle pipetting in 500 µl PBS+2% BSA. This was repeated two times.

Bead Count:

The beads were combined with DSB-X and PBS+2% BSA for a total volume of 100 µl into a 1.5 ml eppendorf tube. The amount of DSB-X added to the beads was dependent upon the total number of beads, and bead size. This was done by beginning with a ratio that saturated 320,250 8 µm beads with 6 µl of DSB labeled protein (determined using flow cytometry and manufacturers specs).

The amount of DSB-X used is calculated as follows:

$$T_{bead\ size} = \text{total number of beads that size}$$

$$SA_{bead\ size} = \text{binding surface area of that bead size}$$

$$\#\ \mu l\ DSB\text{-}X\ \text{to use to label 8 µm beads} = \frac{T_{8micron}}{320250} * 6$$

$$\text{Any other size bead} = \left(\frac{T_{8micron}}{320250} * 6\right) * \left(\frac{T_x * SA_x}{T_{8micron} * SA_{8micron}}\right)$$

The beads were allowed to label for one hour on the rotator at 20 rpm. Bead surface areas can be found in Table 2 below.

TABLE 2

Bead sizes and their surface areas

| Bead Size | Surface Area |
|---|---|
| 8 µm | 201.06 µm$^2$ |
| 10 µm | 314 µm$^2$ |
| 12 µm | 615.75 µm$^2$ |

Final Wash:

The beads were put on a magnet for 5 minutes. Then the supernatant was removed, and gently resuspended in PBS+ 2% BSA 0.5 ml. Then the beads were rotated on a rotator for 5 minutes, placed back on a magnet, and allowed to adhere to one side. Then the supernatant was removed. This was repeated, with the exception of a 10 minute rotation period, and repeated again with a 45 minute rotation period. Finally, the beads were counted and dilutions for plating were calculated.

Release:

Once plated, the ELISpot plate was put on a magnet (magnet not necessary for ELISA). Then 22.5 µl of D-biotin was added per well containing beads. Wells which received other samples the next day were left in the medium. Then the plate was gently placed with a magnet into a 37° C., 5% CO$_2$ incubator, and DSB-X was allowed to release for a minimum of 18 hours. Then the ELISpot images were processed for the purpose of data analysis and interpretation.

Example 6

Preparation of Immunoglobulin-Releasing Reagent Having Polymer Coated Bead

Figure 7:
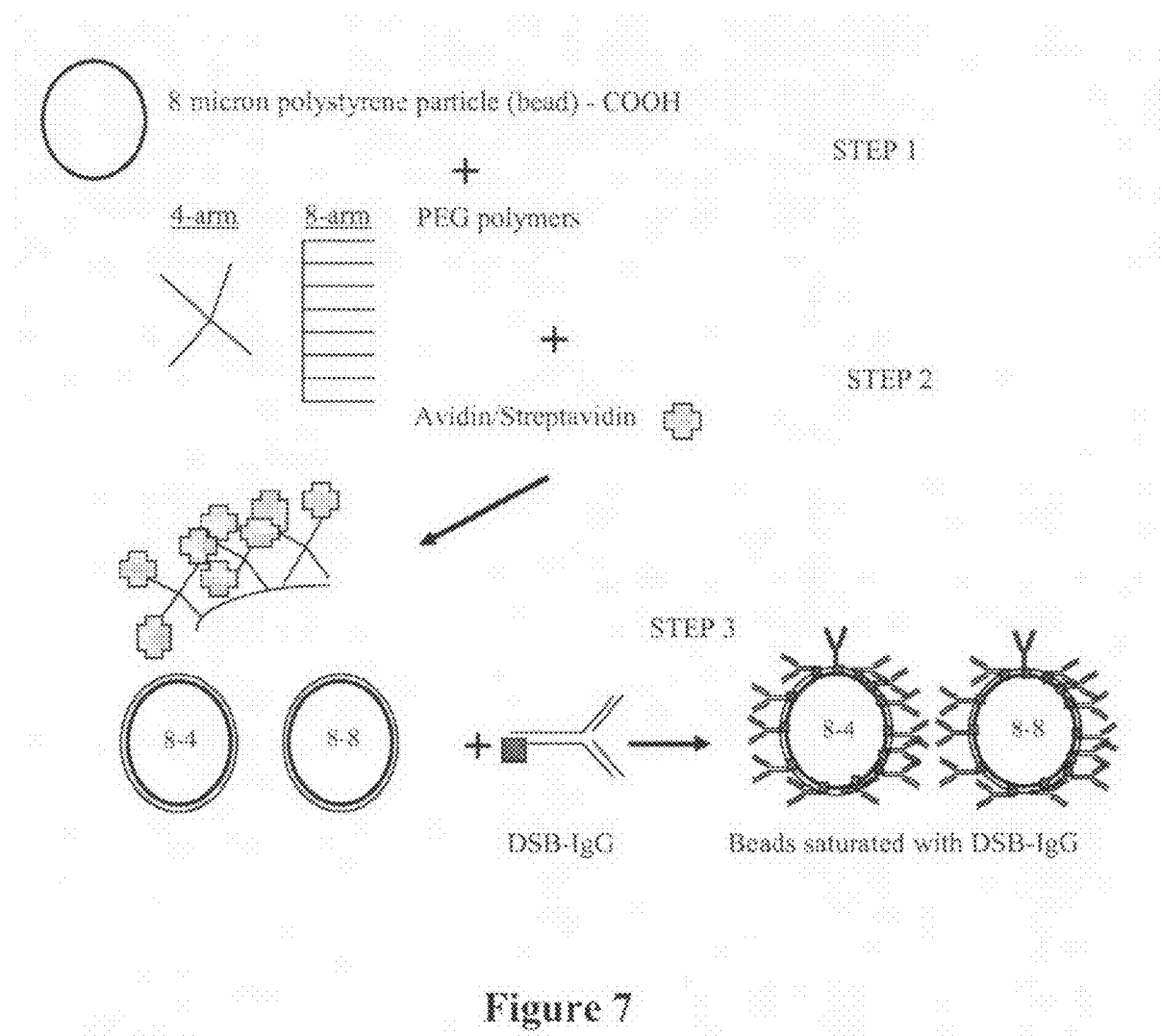
FIG. 7 shows schematically a process for forming an analyte-releasing reagent having beads coated with polymer (polyethylene glycol, designated either "4-arm PEG" or "PEG4"; and "8-arm PEG" or "PEG8") to improve analyte loading. The process is illustrated with exemplary materials used to prepare one preferred IgG-releasing reagent of the present invention.

FIG. 7 shows schematically a process for forming an analyte-releasing reagent having beads coated with polymer (polyethylene glycol, designated either "4-arm PEG" or "PEG4"; and "8-arm PEG" or "PEG8") to improve analyte loading. The process is illustrated with exemplary materials used to prepare one preferred IgG-releasing reagent of the present invention. The preparation of these reagents proceeded in two steps, first conjugation of the polymer to the beads, and then conjugation of streptavidin to the polymer.

Bangs Laboratories carbodiimide-based PolyLink Kit was used to conjugate PEG polymers with amino functional groups on the ends to carboxy-coated or streptavidin coated beads. Polystyrene or latex beads from commercial sources (BangsLab, Micromod) were washed in conjugation buffer (MES pH5.2, 0.05% Proclin 300) from the PolyLink Kit to remove any detergents. The PEG polymers at 10 mg/ml (PEG4=pentaerythritol tetra(aminopropyl) polyoxyethylene, catalog #Sunbright PTE-200PA; and PEG8=hexaglycerol octa(succinimidyloxyglutaryl)polyoxyethylene, catalog #Sunbright HGEO-200GS, both from NOF Corporation, Japan), EDAC carbodiimide (PolyLink kit, Bangs Lab, 4 mg/ml) and Sulfo-NHS (Pierce, Inc. #24510, 11 mg/ml) were weighed and dissolved in conjugation buffer just before use. The beads, at 1×10e5 per sample, were suspended in a total volume of 0.5 ml in conjugation buffer plus EDAC (final concentration 0.4 mg/ml), Sulfo-NHS (final concentration 1.1 mg/ml) and either PEG4 or PEG8 (5 mg/ml final concentration). The beads were mixed gently on a slow rotator for a minimum of 2 hours at room temperature, and washed, first in conjugation buffer, then in pH 6.0 PBS twice. The beads were washed by placing the tubes containing the beads in a magnetic holder. Once the beads settled against the magnet side of the tube, the solution in the tube was carefully removed. The solution was replaced with clean buffer, the tubes removed from the magnet, the beads mixed, and the process repeated to remove the washing solution.

In the second step of the conjugation, 1×10e5 beads per sample were incubated with EDTA and Sulfo-NHS as in the first step, but streptavidin protein (Sigma catalog #S0677 or Pierce Biotechnology catalog #21125) at a concentration of at least 2 mg/ml was combined with the beads instead of PEG polymer. The EDTA, Sulfo-NHS and streptavidin were dissolved in a PBS pH6.0 buffer instead of conjugation buffer for this step. The beads were mixed gently on a rotator for a minimum of two hours at room temperature, and then washed as in the first step. The beads are then ready for counting and coating with DSB-analyte as in the preceding examples.

Beads not being used immediately were stored in PBS+2% w/v BSA (bovine serum albumin, Sigma-Aldrich catalog #A3059-100 g).

Example 7

IgG Bead Release—ELISA and Spot Sizes

Beads of different surface configurations were coated with DSB-IgG and placed in anti-human IgG-coated (Ab from Biosource) ELISA wells at 900 or 600 beads per well. Release into the coated wells was assessed after 48 hrs of incubation with D-biotin, using anti-huIgG-HRP (Jackson Immunoresearch) and ELISA substrate (ABTS, Southern Biotech). Notably, a streptavidin-free detection system (the anti-IgG antibodies) was employed to avoid any risk of false positive results.

Figure 8A:
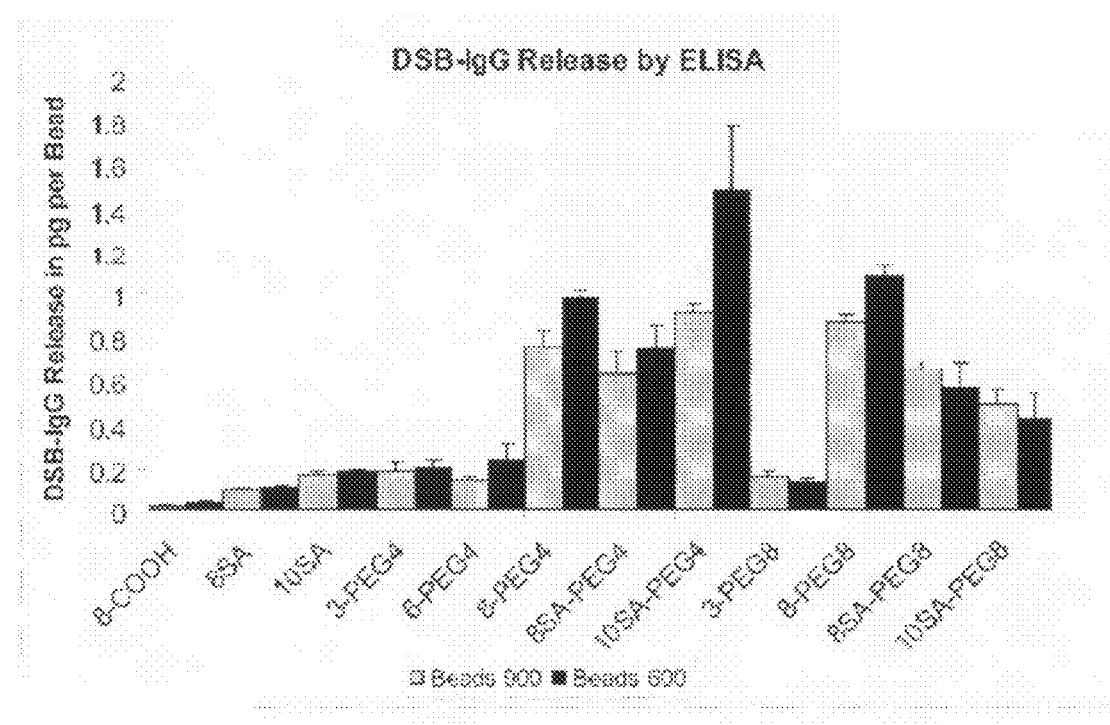
FIGS. 8A-B illustrate IgG release for different constructions of analyte-releasing reagents, as measured by ELISA and ELISpot.

Results are expressed in picograms (pg) IgG released/bead (FIG. 8A). DSB-IgG was released from streptavidin coated beads of various diameters (in microns) (3SA, 6SA, 8SA, 10SA). Much higher amounts of DSB-IgG were released by beads with polyethylene glycol linking streptavidin to the carboxy-embedded plastic beads (8PEG4, 8PEG8). Even higher amounts were released from beads formed by PEG-linking streptavidin to beads already coated by streptavidin (8SA-PEG4, 8SA-PEG8, 10SA-PEG4, 10SA-PEG8). Beads designated 8COOH are 8 micron beads without the streptavidin coat.

Figure 8B:
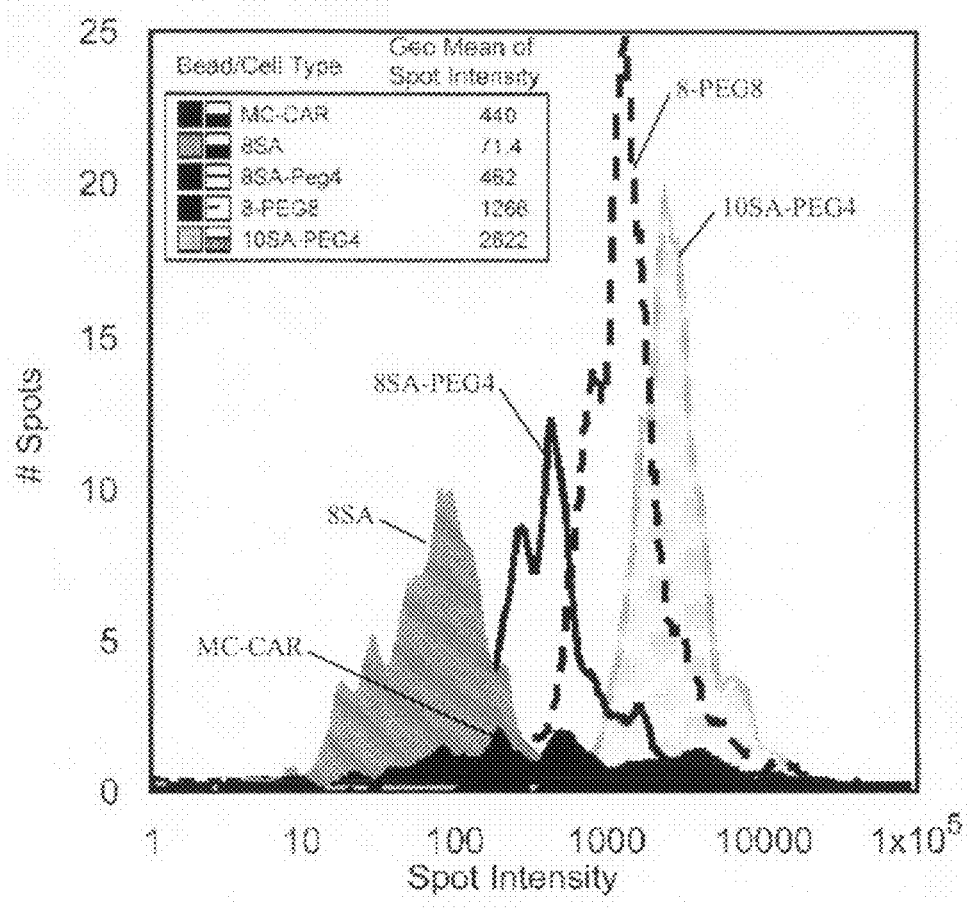

All of these beads were also assessed for spot production by ELISpot (capture Ab from Biosource, anti-huIgG-AP from Jackson Immunoresearch and substrate from Vector (AP substrate kit III)). Analysis was carried out using ExploraSpot (Mossman laboratory, University of Rochester, Rochester, N.Y.), and FLOWJO™ (Tree Star, Inc., Ashland, Oreg.) programs. Choosing four of these bead types to use as a "standard curve" for IgG release (8SA, 8SA-PEG4, 8-PEG8, and 10SA-PEG4), a set of beads was selected so as to span the size of IgG spots produced by the myeloma cell line MC-CAR (FIG. 8B).

Example 8

Standard Curve Generation

Figure 9A:
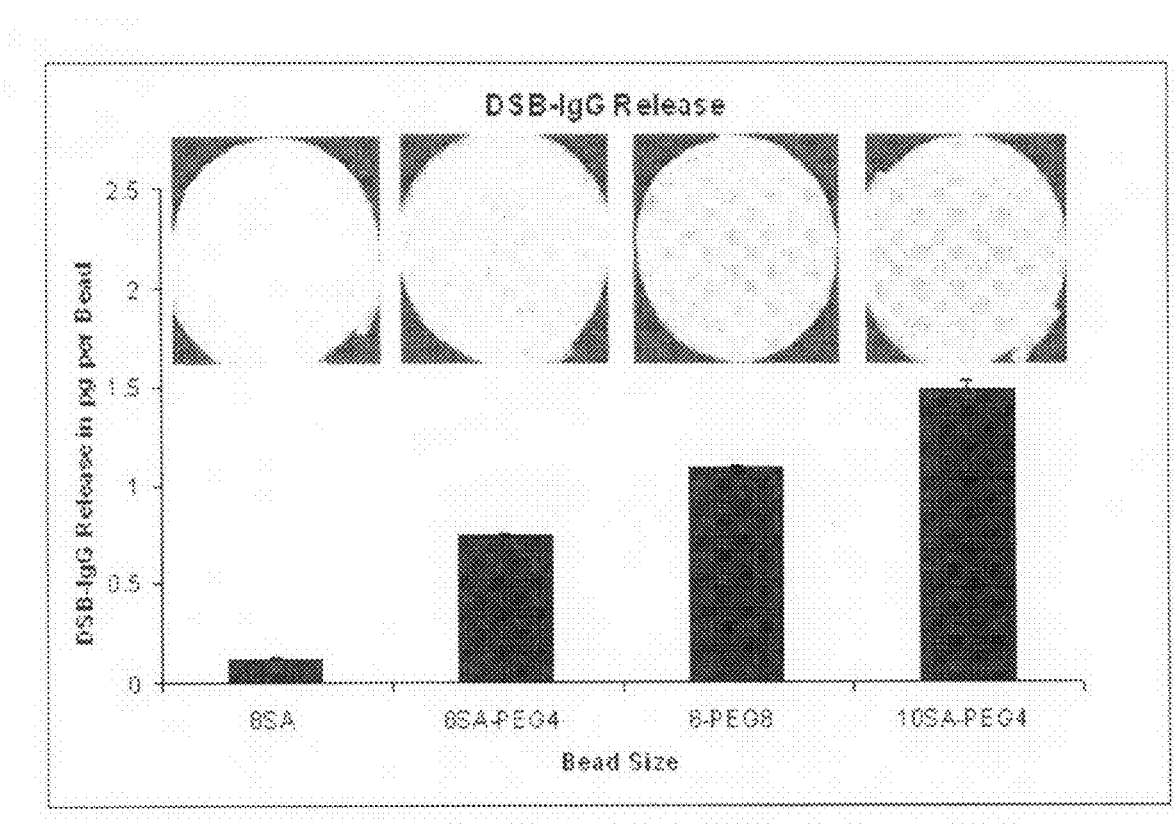
FIGS. 9A-B show the ELISpot results for DSB-IgG release for the mixture of four IgG-releasing reagents identified in FIG. 8B (FIG. 9A), and the corresponding standard curve generated therefrom (FIG. 9B). The standard curve can be used to calculate the amount of IgG released by cells based on the measured spot volume density and the standard curve for bead release.
Figure 9B:
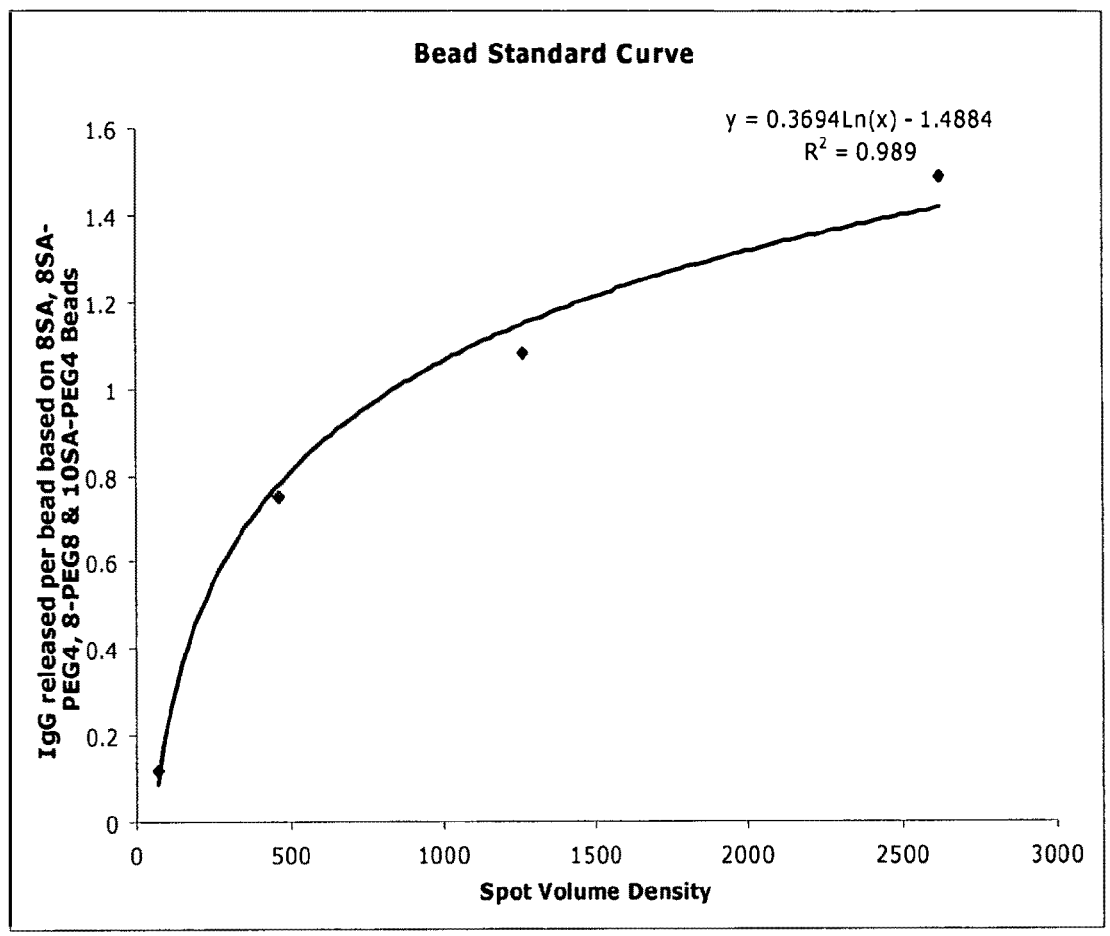

Using four bead types identified in Example 7, the mean spot size was compared with the amount of IgG released per bead (FIG. 9A) to generate the standard curve shown in FIG. 9B.

Example 9

IgG Released by MC-CAR Cells

Figure 10:
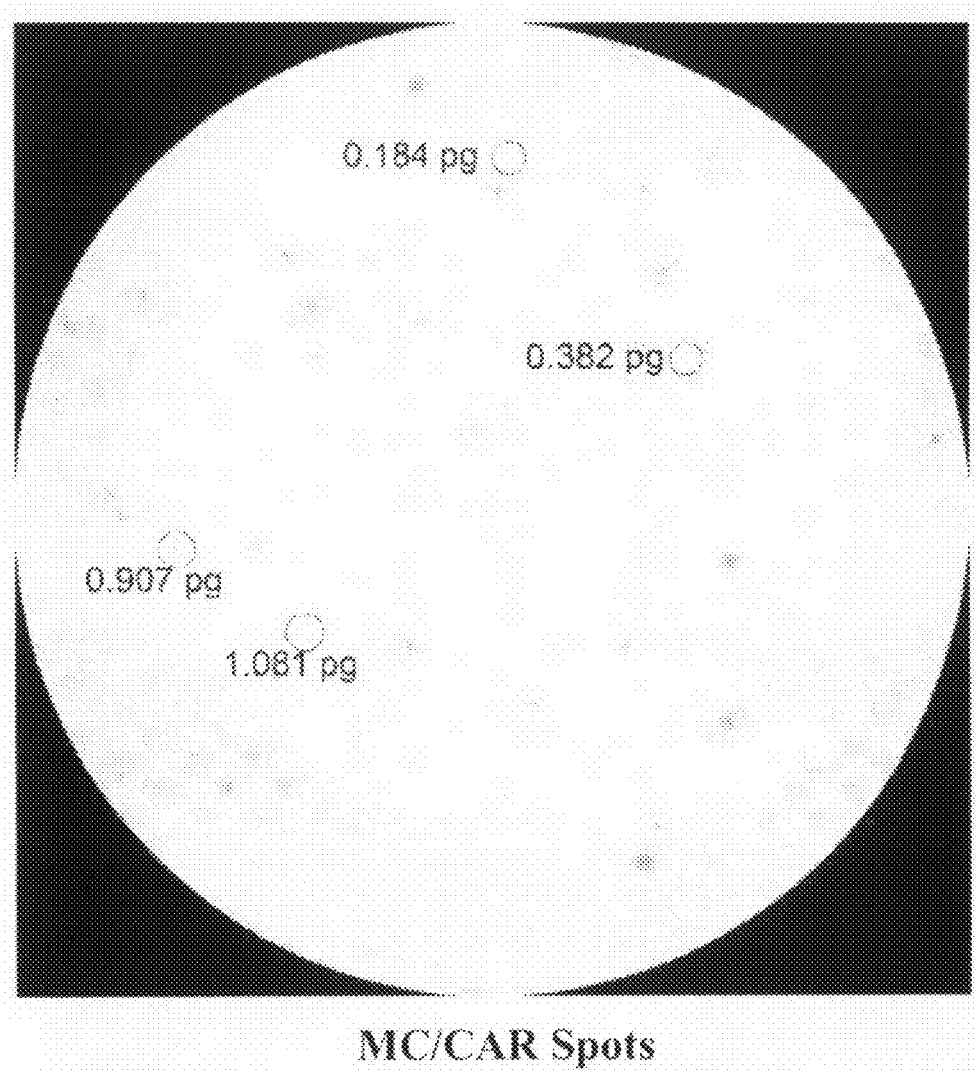
FIG. 10 shows IgG secretion rates for individual MC-CAR myeloma cells following 24 hour secretion study. Rates are in pg per cell.

Using the standard curve generated in Example 8, with the bead-released DSB-IgG spots, the amount of IgG in spots made by MC-CAR myeloma cells was quantified. These results are shown in FIG. 10. Based on the size and density of the spots produced by MC-CAR cells, it was determined that IgG secretions varied widely from cell to cell. Quantified spots, representing 0.184 pg to 1.081 pg per cell, are illustrated.

Example 10

DSB-IgG Released from Beads can Generate Spots with or Without Capture Antibody

Figure 11A:
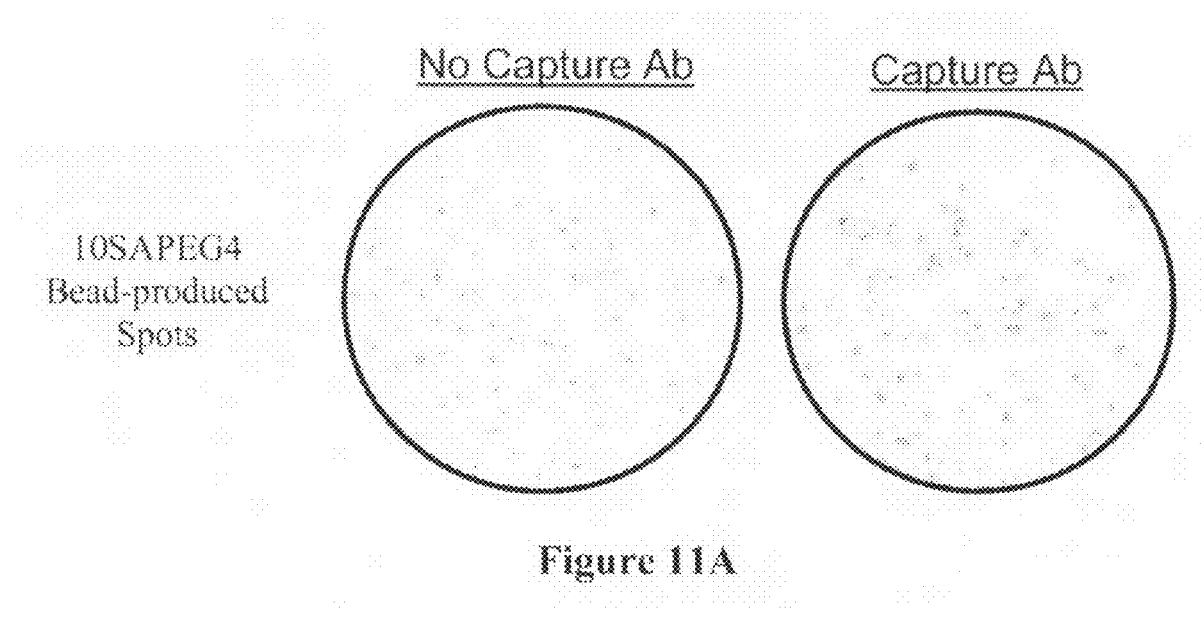
FIG. 11A shows spots of IgG, produced by 10SA-PEG4 beads and detected following secretion into wells either precoated with capture antibody or without capture antibody.
Figure 11B:
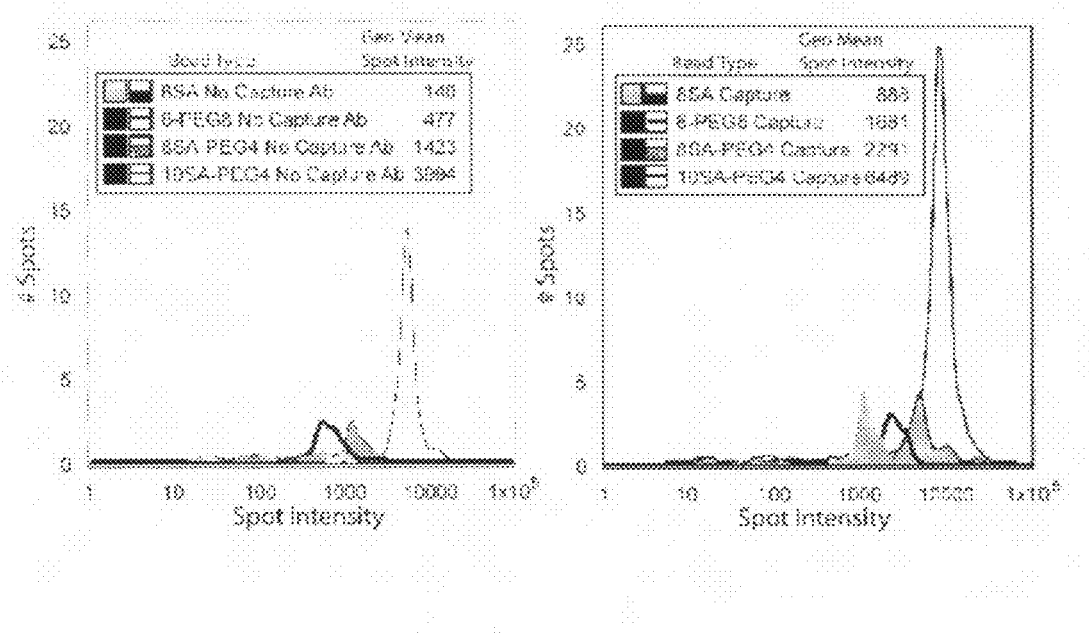
FIG. 11B shows the histogram for results obtained using the four different types of beads (8SA, 8SA-PEG4, 8-PEG8, and 10SA-PEG4), both with and without capture antibody.

The necessity of using a capture antibody was assessed. DSB-IgG coated beads were placed into ELISpot wells pre-wetted with 35% ethanol, washed with PBS and coated with PBS (no capture) or with anti-human IgG capture antibody. The DSB-IgG was released with D-biotin and developed as in Example 7 (using the anti-IgG detection antibody). Representative results are shown in FIG. 11A for release by 10SA-PEG4 reagent. Visually, the results are comparable. When measured using the procedures described above for plate analysis (see Example 7), the raw data shows a slight decrease in the numbers of spots per well per bead type (i.e., each of 8SA, 8-PEG8, 8SA-PEG4, and 10SA-PEG4 reagents). Because spots were produced even without capture antibody, these results indicate that the capture antibody is not required for simple detection of the analyte, but should be present to ensure valid comparison with spots produced by cells which secrete many different proteins and thus benefit more from the use of a capture antibody.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of quantifying cellular secretion of an analyte comprising:
    providing a container comprising a surface capable of binding an analyte;
    providing a standard curve for release of the analyte into a container by one or more analyte-releasing reagents that comprise a bead and the analyte releasably bound to the bead, the container comprising a surface capable of binding the analyte;
    introducing into the provided container one or more cells that secrete the analyte;
    detecting the presence of analyte bound to the surface of the container into which the one or more cells were introduced; and
    comparing the detected analyte to the standard curve to quantify the amount of analyte released by the one or more cells.

2. The method according to claim 1, wherein said providing a standard curve comprises detecting analyte released by three or more analyte-releasing reagents each characterized, on average, by a different amount of bound analyte that is between about 0.01 picograms up to about 10 micrograms.

3. The method according to claim 1 wherein the bead further comprises a linker molecule comprising a first portion tethered to the bead and a second portion bound to the analyte.

4. The method according to claim 3 wherein the linker molecule is cleavable.

5. The method according to claim 4 wherein the linker molecule is enzymatically cleavable or photo-cleavable.

6. The method according to claim 4, wherein the linker molecule is a peptide or polypeptide, polysaccharide, double-stranded nucleic acid molecule, or a compound having a photoreactive moiety.

7. The method according to claim 3 wherein the first and second portions of the linker molecule are capable of reversibly binding to one another.

8. The method according to claim 7 wherein the first and second portions each comprise single-stranded nucleic acid molecules capable of hybridizing to one another.

9. The method according to claim 8 wherein release of the analyte comprises heating the analyte-releasing reagent to a temperature close to, at, or above the melting temperature of the nucleic acid molecules of the first and second portions.

10. The method according to claim 7 wherein the first and second portions are molecules that have an affinity for binding to one another.

11. The method according to claim 10 wherein release of the analyte comprises introducing a displacing molecule that has an affinity for the first or second portion of the linker molecule that is greater than the affinity between the first and second portions.

12. The method according to claim 7 wherein the first and second portions are electrochemically associated.

13. The method according to claim 12 wherein release of the analyte comprises adjusting the pH to dissociate the first and second portions.

14. The method according to claim 3 further comprising a polymer coating applied to a surface of the bead, wherein the first portion of the linker molecule is bound directly to the polymer coating.

15. The method according to claim 14 wherein the polymer coating is formed by a polymer selected from the group consisting of polyethylene glycol, dextran, chitosan, acrylamide, cellulose, methacrylate, oxazoline, methacryloxyethyltrimethylammonium, methylpyridine, cinylpyridine, allylamine, butadiene/maleic acid, polyethylene oxide, vinylpyrrolidone, polystyrene, polyvinyl acetate, polyethylenimine, polypropylene, and pullalan.

16. The method according to claim 1, wherein said providing the standard curve is carried out in parallel with said introducing.

17. The method according to claim 1, wherein said providing the standard curve is carried out using one or more containers pre-coated with analyte released by the analyte-releasing reagent.

18. The method according to claim 1 wherein said providing a standard curve is carried out prior to said introducing and detecting.

19. The method according to claim 1 further comprising:
first washing the container prior to said detecting, whereby said first washing is effective substantially to remove the one or more cells from the container.

20. The method according to claim 19 wherein said detecting comprises:
providing a detection molecule that binds to the analyte and includes a detectable label; and
introducing the detection molecule into the container after said first washing.

21. The method according to claim 20 wherein the detectable label is a fluorophore, an enzymatic label, or a radiolabel.

22. The method according to claim 21 wherein said detecting comprises measuring a signal directly caused or indirectly induced by the detectable label bound to the container surface.

23. The method according to claim 19 further comprising:
second washing the container after said introducing the detection molecule and prior to said detecting, whereby said second washing is effective substantially to remove from the container the detection molecule that remains unbound to the analyte after said introducing.

24. The method according to claim 1 wherein the provided container further comprises one or more capture molecules bound to the surface, wherein the one or more capture molecules selectively bind to the analyte.

25. The method according to claim 24 wherein the one or more capture molecules are selected from the group consisting of antibodies, antibody mimics, antigens, peptides, proteins, lipids, polysaccharides, oligonucleotides, nucleic acids, protein-binding ligands, receptors, chemical compounds, cell fragments, cellular substructures, synapses, cell organelles, cancer cells, tissue samples, viruses, and bacteria.

26. The method according to claim 1 wherein the analyte is a product secreted or released by a cell or a drug delivery vehicle.

27. The method according to claim 1, wherein the analyte-releasing reagent comprises a plurality of distinct populations of beads to which the analyte is releasably bound, wherein the distinct populations comprises at least three different bead populations loaded with different amounts of the analyte.

28. A method of determining release rate of a drug from a drug delivery vehicle, the method comprising:
providing a container comprising a surface capable of binding a drug;
providing a standard curve for rate of drug release into a container by one or more drug-releasing reagents that comprise a bead and the drug releasably bound to the bead, the container comprising a surface capable of binding the drug;
introducing into the provided container a drug delivery vehicle that releases the drug over a period of time;
detecting the presence of drug bound to the surface of the container into which the drug delivery vehicle was introduced; and
comparing the detected amount of drug to the standard curve to qualify the rate of drug release by the drug delivery vehicle.

29. A method of quantifying cellular secretion of an analyte comprising:
providing a standard curve for release of an analyte into a first container by one or more analyte-releasing reagents that comprise a bead and the analyte releasably bound to the bead, the first container comprising a surface capable of binding the analyte;
introducing one or more cells that secrete the analyte into a second container comprising a surface capable of binding the analyte;
detecting the presence of analyte bound to the surface of the second container; and
comparing the detected analyte to the standard curve to quantify the amount of analyte released by the one or more cells.

30. A method of determining release rate of a drug from a drug delivery vehicle, the method comprising:
providing a standard curve for release of a drug into a first container by one or more drug-releasing reagents that comprise a bead and the drug releasably bound to the bead, the first container comprising a surface capable of binding the drug;
introducing a drug delivery vehicle that releases the drug over a period of time into a second container comprising a surface capable of binding the drug;
detecting the presence of drug bound to the surface of the second container; and
comparing the detected amount of drug to the standard curve to qualify the rate of drug release by the drug delivery vehicle.

* * * * *